US009585992B2

(12) United States Patent
Bene

(10) Patent No.: US 9,585,992 B2
(45) Date of Patent: Mar. 7, 2017

(54) APPARATUS AND METHOD FOR DETERMINING A PARAMETER INDICATIVE OF THE PROGRESS OF AN EXTRACORPOREAL BLOOD TREATMENT

(71) Applicant: Gambro Lundia AB, Lund (SE)

(72) Inventor: Bernard Bene, Irigny (FR)

(73) Assignee: Gambro Lundia AB, Lund (SE)

( * ) Notice: Subject to any disclaimer, the term of this patent is extended or adjusted under 35 U.S.C. 154(b) by 297 days.

(21) Appl. No.: 14/415,095

(22) PCT Filed: Jun. 14, 2013

(86) PCT No.: PCT/IB2013/054875
§ 371 (c)(1),
(2) Date: Jan. 15, 2015

(87) PCT Pub. No.: WO2014/013358
PCT Pub. Date: Jan. 23, 2014

(65) Prior Publication Data
US 2015/0129499 A1    May 14, 2015

Related U.S. Application Data

(60) Provisional application No. 61/672,898, filed on Jul. 18, 2012.

(30) Foreign Application Priority Data

Jul. 18, 2012  (EP) .................................... 12005255

(51) Int. Cl.
*A61M 1/16*       (2006.01)

(52) U.S. Cl.
CPC ............ *A61M 1/1609* (2014.02); *A61M 1/16* (2013.01); *A61M 1/1605* (2014.02); *A61M 1/1607* (2014.02); *A61M 1/1613* (2014.02); *A61M 1/1617* (2014.02)

(58) Field of Classification Search
None
See application file for complete search history.

(56) References Cited

U.S. PATENT DOCUMENTS

| | | |
|---|---|---|
| 5,024,756 A | 6/1991 | Sternby |
| 5,100,554 A | 3/1992 | Polaschegg |

(Continued)

FOREIGN PATENT DOCUMENTS

| | | |
|---|---|---|
| CA | 2336923 | 1/2000 |
| DE | 19649775 | 6/1998 |

(Continued)

OTHER PUBLICATIONS

International Search Report and Written Opinion issued Oct. 16, 2013, for related International Appln. No. PCT/IB2013/054875.

(Continued)

*Primary Examiner* — Chester Barry
(74) *Attorney, Agent, or Firm* — K&L Gates LLP

(57) ABSTRACT

An apparatus for extracorporeal treatment of blood (1) comprising a treatment unit (2), a blood withdrawal line (6), a blood return line (7), a preparation line (19) and a spent dialysate line (13). A control unit (10) is configured to calculate values of a parameter relating to treatment effectiveness based on measures of the conductivity in the spent dialysate line (13) subsequent to an alternating conductivity perturbation continuously imposed on the preparation line (19) of fresh dialysis fluid.

30 Claims, 7 Drawing Sheets

(56) References Cited

U.S. PATENT DOCUMENTS

| | | | |
|---|---|---|---|
| 5,567,320 | A | 10/1996 | Goux et al. |
| 6,110,384 | A | 8/2000 | Goux et al. |
| 6,187,199 | B1 | 2/2001 | Goldau |
| 6,602,424 | B1 | 8/2003 | Kramer et al. |
| 2001/0004523 | A1 | 6/2001 | Bosetto et al. |
| 2007/0131595 | A1 | 6/2007 | Jansson et al. |

FOREIGN PATENT DOCUMENTS

| | | |
|---|---|---|
| EP | 0547025 | 6/1996 |
| EP | 0658352 | 10/1997 |
| EP | 0920877 | 6/1999 |
| EP | 2380609 | 10/2011 |
| FR | 2713936 | 6/1995 |
| WO | 2012127298 | 9/2012 |

OTHER PUBLICATIONS

International Search Report—PCT/IB2013/059711—Mailing date Apr. 14, 2014—5 pages.
Written Opinion—PCT/IB2013/059711—Mailing date Apr. 14, 2014—8 pages.
International Search Report—PCT/IB2013/060984—Dated Jul. 7, 2014—2 pages.
European Search Report—EP Application No. 12198335.7-1651—Dated May 23, 2013—7 pages.
Gotch et al., "A mechanistic analysis of the National Cooperative Dialysis Study (NCDS)", Kidney International, 1985, vol. 28, pp. 526-534.

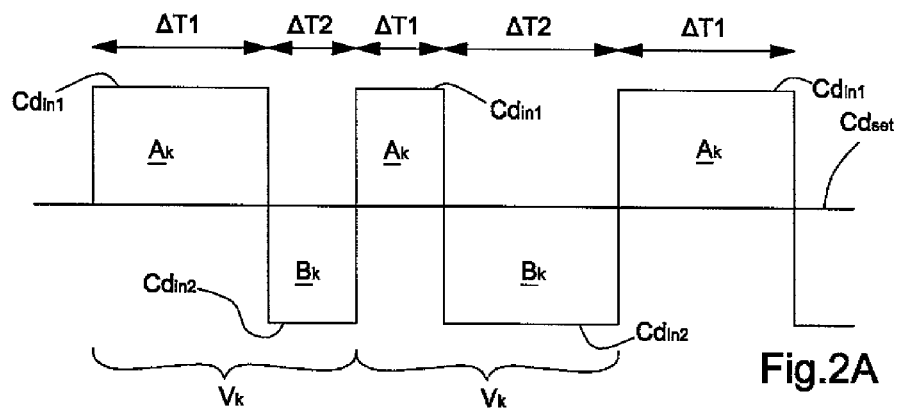
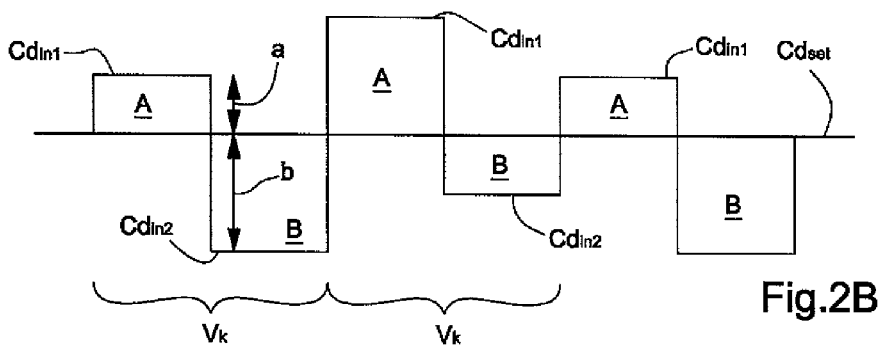
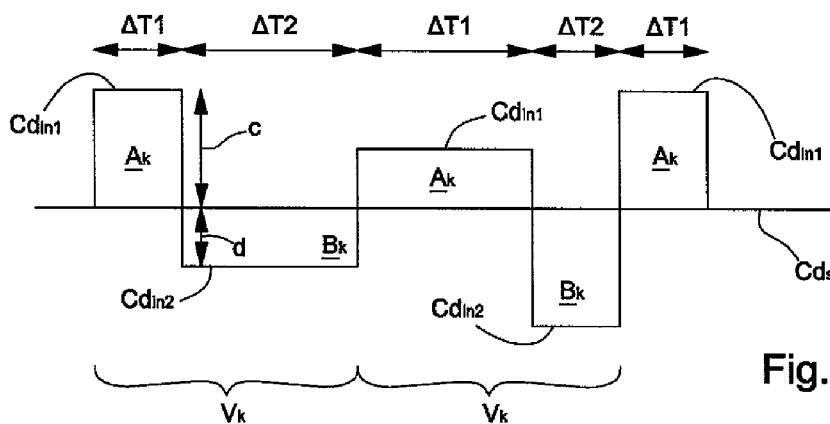

APPARATUS AND METHOD FOR DETERMINING A PARAMETER INDICATIVE OF THE PROGRESS OF AN EXTRACORPOREAL BLOOD TREATMENT

CROSS REFERENCE TO RELATED APPLICATIONS

The present application is a National Stage of International Application No. PCT/IP2013/054875, filed on Jun. 14, 2013, which claims priority to European Patent Application No. 12005255.0, filed Jul. 18, 2012, and U.S. Provisional Application No. 61/672,898, filed Jul. 18, 2012, the entire contents of which are being incorporated herein by reference.

The invention relates to an apparatus and to a method for determining a parameter indicative of the progress of an extracorporeal blood treatment, in particular a purification treatment whose purpose is to alleviate renal insufficiency, such as haemodialysis or haemodiafiltration.

In an haemodialysis treatment a patient's blood and a treatment liquid approximately isotonic with blood flow are circulated in a respective compartment of haemodialyser, so that, impurities and undesired substances present in the blood (urea, creatinine, etc.) may migrate by diffusive transfer from the blood into the treatment liquid. The ion concentration of the treatment liquid is chosen so as to correct the ion concentration of the patient's blood.

In a treatment by haemodiafiltration, a convective transfer by ultrafiltration, resulting from a positive pressure difference created between the blood side and the treatment-liquid side of the membrane, is added to the diffusive transfer obtained by dialysis.

It is of interest to be able to determine, throughout a treatment session, one or more parameters indicative of the progress of the treatment so as to be able, where appropriate, to modify the treatment conditions that were initially fixed or to at least inform the patient and the medical personnel about the effectiveness of the treatment.

The knowledge of one or more of the following parameters may make it possible to follow the progress of the treatment, and for instance may allow to assess the suitability of the initially fixed treatment conditions:

the concentration in the blood of a given solute (for example, sodium), the actual dialysance D or the actual clearance K of the exchanger for solute (the dialysance D and the clearance K representing the purification efficiency of the exchanger), the dialysis dose administered after a treatment time t, which, according to the work of Sargent and Gotch, may be linked to the dimensionless ratio Kt/V, where K is the actual clearance in the case of urea, t the elapsed treatment time and V the volume of distribution of urea, i.e. the total volume of water in the patient (Gotch F. A. and Sargent S. A., "A mechanistic analysis of the National Cooperative Dialysis Study (NCDS)", Kidney Int. 1985, Vol. 28, pp. 526-34).

The determination of these parameters requires precise knowledge of a physical or chemical characteristic of the blood. As it can be understood, determination of this characteristic cannot in practice be obtained by direct measurement on a specimen for therapeutic, prophylactic and financial reasons. Indeed, it is out of the question taking multiple specimens necessary to monitor the effectiveness of the treatment from a patient who is often anemic; furthermore, given the risks associated with handling specimens of blood which may possibly be contaminated, the general tendency is to avoid such handling operations; finally, laboratory analysis of a specimen of blood is both expensive and relatively lengthy, this being incompatible with the desired objective of knowing the effectiveness of a treatment while the treatment is still ongoing. Several methods have been proposed for in vivo determining haemodialysis parameters without having to take measurements on blood samples.

Document EP 0547025 describes a method for determining the concentration of a substance, such as sodium, in a patient's blood subjected to a haemodialysis treatment. This method also makes it possible to determine the dialysance D—for example for sodium—of the haemodialyser used. The method comprises the steps of circulating a first and a second haemodialysis liquids having different sodium concentrations in succession through the haemodialyser, measuring the conductivity of the first and second dialysis liquids upstream and downstream of the haemodialyser, and computing the concentration of sodium in the patient's blood (or the dialysance D of the haemodialyser for sodium) from the values of the conductivity of the liquid which are measured in the first and second dialysis liquids upstream and downstream of the haemodialyser. Document EP 0658352 describes another method for the in vivo determination of haemodialysis parameters, which comprises the steps of: making at least a first and a second treatment liquids, having a characteristic (the conductivity, for example) associated with at least one of the parameters (the ion concentration of the blood, the dialysance D, the clearance K, Kt/V, for example) indicative of the treatment, flow in succession through the haemodialyser, the value of the characteristic in the first liquid upstream of the exchanger being different from the value of the characteristic in the second liquid upstream of the exchanger; measuring, in each of the first and second treatment liquids, two values of the characteristic, respectively upstream and downstream of the exchanger; making a third treatment liquid flow through the exchanger while the characteristic of the second liquid has not reached a stable value downstream of the exchanger, the value of the characteristic in the third liquid upstream of the exchanger being different from the value of the characteristic in the second liquid upstream of the exchanger; measuring two values of the characteristic in the third liquid, respectively upstream and downstream of the exchanger; and computing at least one value of at least one parameter indicative of the progress of the treatment from the measured values of the characteristic in the first, second and third treatment liquids.

Another method for the in vivo determination of the haemodialysis parameters which does not require taking measurements on blood samples is described in document EP 0920877. This method includes the steps of: making a treatment liquid flow through the exchanger, this treatment liquid having a characteristic which has an approximately constant nominal value upstream of the exchanger; varying the value of the characteristic upstream of the exchanger and then re-establishing the characteristic to its nominal value upstream of the exchanger; measuring and storing in memory a plurality of values adopted by the characteristic of the treatment liquid downstream of the exchanger in response to the variation in the value of this characteristic caused upstream of the exchanger; determining the area of a downstream perturbation region bounded by a baseline and a curve representative of the variation with respect to time of the characteristic; and computing the parameter indicative of the effectiveness of a treatment from the area of the downstream perturbation region and from the area of an upstream perturbation region bounded by a baseline and a curve representative of the variation with respect to time of the characteristic upstream of the exchanger. The above described methods require a relatively short—compared to treatment time—modification of the value of a characteristic of the dialysis liquid (the conductivity, for example) and then the re-establishment of this characteristic to its initial value, which is generally the prescribed value. Since, deviations from the prescription are not desirable and since the above described methods require a minimum duration of the introduced modification, it derives that all these methods can be carried out only few times during a treatment.

With the aim of further improving the above methods, document U.S. 2001004523 describes a solution for continuously determining a parameter (D, Cbin, K, Kt/V) indicative of the effectiveness of an extracorporeal blood treatment comprising the steps of: causing a succession of sinusoidal variations in the characteristic (Cd) a treatment liquid upstream of the exchanger, continuously storing in memory a plurality of values ($Cd_{in1} \ldots Cd_{inj} \ldots Cd_{inp}$) of the characteristic (Cd) upstream of the exchanger, measuring and continuously storing in memory a plurality of values ($Cd_{out1} \ldots Cd_{outj} \ldots Cd_{outp}$) adopted by the characteristic (Cd) downstream of the exchanger in response to the variations in the characteristic (Cd) which are caused upstream of the exchanger, computing—each time that a predetermined number of new values ($Cd_{outj}$) of the characteristic (Cd) downstream of the exchanger has been stored—a parameter (D, Cbin, K, Kt/V) indicative of the effectiveness of the extracorporeal blood treatment, from a first series of values ($Cd_{inj}$) of the characteristic (Cd) upstream of the exchanger, from a second series of values ($Cd_{outj}$) of the characteristic (Cd) downstream of the exchanger, based on a mathematical model of the influence of the characteristic (Cd) on the effectiveness of the treatment.

The advantage of a sinusoidal perturbation in the characteristic of the liquid upstream the dialyzer is that the patient may not be exposed to a treatment liquid very different from the prescribed treatment liquid (for example, one which is too rich or too depleted in sodium).

Although the above method resulted in certain improvements over the state of the art, the applicant uncovered that generating sinusoidal type perturbations in the dialysis liquid may not be easily doable. Moreover, the accuracy of the parameter determination is strictly correlated to the mathematical model adopted. Furthermore, the characteristic in the liquid downstream the dialyzer may be difficult to accurately be measured due to a number of factors. First, a sinusoidal perturbation never leads to any equilibrium state so it is difficult to properly interpret sensor detections. Moreover, the hydraulic delay, the damping effect caused by the dialyzer, and the noise introduced by the machine and its components may render further difficult interpretation of the signals detected by the sensors, particularly in presence of a continuously varying perturbation.

It is therefore an object of the present invention to provide an apparatus and a method to reliably calculate an effectiveness parameter a plurality of times during treatment without substantially impairing on the treatment prescription.

Moreover, it is an auxiliary object providing a method and an apparatus which are not very sensitive to incidents or noise or accidental detection errors which may arise during the measurement of an isolated value or of a sinusoidal perturbation and which may falsify the subsequent computations.

Additionally, it is an object providing a method and an apparatus which may be implemented with no need of high computational power and without complex mathematical models.

Another auxiliary object is an apparatus capable of operating in a safe manner.

A further auxiliary object is an apparatus capable of automatically calculate the parameter and inform the operator accordingly.

SUMMARY

At least one of the above objects is substantially reached by an apparatus according to one or more of the appended claims.

Apparatus and processes according to aspects of the invention and capable of achieving one or more of the above objects are here below described.

A $1^{st}$ aspect relates to an apparatus for extracorporeal treatment of blood comprising: a preparation line having one end configured for being connected to an inlet of a secondary chamber of a treatment unit having a primary chamber and said secondary chamber separated by a semi-permeable membrane;
   a spent dialysate line having one end configured for being connected to an outlet of said secondary chamber;
   a control unit configured for commanding execution of the following steps:
      causing a treatment liquid to flow in the preparation line to the secondary chamber, the treatment liquid having a characteristic (Cd) which is one selected in the group of:
         conductivity of the treatment liquid,
         concentration of at least one substance in the treatment liquid;
      receiving at least one prescription value ($Cd_{set}$) for the characteristic (Cd);
      causing a plurality of consecutive and continuously repeated variations ($V_k$) of the characteristic (Cd) around the prescription value ($Cd_{set}$) in the liquid flowing in the preparation line, each one of said variations being obtained by:
         changing the value of the characteristic (Cd) in the preparation line until a first inlet value ($Cd_{in1}$) of the characteristic is reached, said first value ($Cd_{in1}$) being different from the prescription value ($Cd_{set}$),
         keeping the characteristic (Cd) in the preparation line unchanged at said first inlet value ($Cd_{in1}$) during a first time interval ($\Delta T_1$),
         changing the value of the characteristic (Cd) in the preparation line until a second inlet value ($Cd_{in2}$) of the characteristic is reached, wherein the second inlet value ($Cd_{in2}$) is different than the prescription value ($Cd_{set}$) and the prescription value ($Cd_{set}$) is comprised between said first and said second inlet values ($Cd_{in1}$; $Cd_{in2}$),
         keeping the characteristic (Cd) in the preparation line unchanged at said second inlet value ($Cd_{in2}$) during a second time interval ($\Delta T_2$) following the first time interval, during each of said variations ($V_k$) the characteristic (Cd) in the liquid flowing in the preparation line taking the first inlet value ($Cd_{in1}$) during the first time interval ($\Delta T_1$) and taking the second inlet value ($Cd_{in2}$) during the second time interval ($\Delta T_2$);

for of each of said variations ($V_k$):
  receiving measures of a first and second outlet values ($Cd_{out1}$, $Cd_{out2}$) respectively adopted by the characteristic (Cd) in the spent dialysate line in response to the first and second inlet values ($Cd_{in1}$; $Cd_{in2}$) taken by the same characteristic in the preparation line, and
  computing at least one value of a parameter (D, $Cb_{in}$, K, K·t/V) indicative of the effectiveness of the extracorporeal blood treatment from said first and second outlet values ($Cd_{out1}$, $Cd_{out2}$) taken by the characteristic (Cd) in the spent dialysate line.

In a $2^{nd}$ aspect according to the 1st aspect, the first time interval ($\Delta T1$) and the second time interval ($\Delta T2$) of each variation ($V_k$) have same duration.

In a $3^{rd}$ aspect according to any one of the preceding aspects, the first and second inlet values (Cdin1, Cdin2) in each variation ($V_k$) differ from the prescribed value (Cdset) by a same quantity.

In a $4^{th}$ aspect according to any one of the preceding aspects, the first and second inlet values (Cdin1, Cdin2) in each variation ($V_k$) differ from the prescribed value (Cdset) by a same quantity comprised between 0.3 and 1 mS/cm.

In a $5^{th}$ aspect according to any one of the preceding aspects, the first and second inlet values (Cdin1, Cdin2) in each variation ($V_k$) define a sequence of variations ($V_k$) symmetrically evolving around the prescribed value.

In a $6^{th}$ aspect according to any one of the preceding aspects, the control unit is further configured for receiving a total treatment time (T), and wherein said variations ($V_k$) of the characteristic (Cd) around the prescription value ($Cd_{set}$) are consecutively and continuously repeated during a significant portion of the treatment time (T) such that a plurality of values of the parameter (D, $Cb_{in}$, K, K·t/V) indicative of the effectiveness of the extracorporeal blood treatment are correspondingly determined.

In a $7^{th}$ aspect according to the $6^{th}$ aspect, said significant portion of the treatment time is at least 25% of said treatment time (T) optionally at least 50% of said treatment time (T).

In a $8^{th}$ aspect according to the $6^{th}$ aspect, said significant portion of the treatment time is at least 75% of said treatment time (T), optionally said significant portion of the treatment time is the entire treatment time (T).

In a $9^{th}$ aspect according to any one of the preceding aspects, the second time interval ($\Delta T_2$) in each variation is immediately following the respective first time interval.

In a $10^{th}$ aspect according to any one of the preceding aspects, the step of causing a plurality of consecutive and continuously repeated variations ($V_k$) of the characteristic (Cd) around the prescription value ($Cd_{set}$) is configured such that, taking as base line the line defined over time by the prescribed value ($Cd_{set}$), the sum of the areas ($A_k$) formed between said base line and the portions of curve representative of the inlet conductivity/concentration positioned above the base line is identical or close to the sum of the areas ($B_k$) defined between the base line and the portions of curve representative of the inlet conductivity/concentration curve positioned below the base line. This allows the respect of the prescription value ($Cd_{set}$) across the treatment irrespective of the continuous conductivity/concentration variations imposed to the inlet conductivity.

In a $11^{th}$ aspect according to any one of the preceding aspects, each first time interval ($\Delta T_1$) and each second time interval ($\Delta T_2$) in each variation is longer than 2 minutes and shorter than 6 minutes.

In a $12^{th}$ aspect according to any one of the preceding aspects, changing the value of the characteristic (Cd) in the preparation line until a first inlet value ($Cd_{in1}$) of the characteristic is reached comprises a step increase or a step decrease of the characteristic, and wherein changing the value of the characteristic (Cd) in the preparation line until a second inlet value ($Cd_{in2}$) of the characteristic is reached comprises a step decrease or a step increase of the characteristic such that the consecutive and continuously repeated variations ($V_k$) define a square wave.

In a $13^{th}$ aspect according to any one of the preceding aspects, at each variation ($V_k$) said change of the value of the characteristic (Cd) until a first inlet value ($Cd_{in1}$) is reached is an increase of the value of the characteristic (Cd) above the prescription value ($Cd_{set}$) or a decrease of the value of the characteristic (Cd) below the prescription value ($Cd_{set}$).

In a $14^{th}$ aspect according to any one of the preceding aspects, at each variation ($V_k$) said change of the value of the characteristic (Cd) until a second inlet value ($Cd_{in2}$) is reached is a decrease of the value of the characteristic (Cd) below the prescription value ($Cd_{set}$) when the first value ($Cd_{in1}$) is above the prescription value ($Cd_{set}$) or an increase of the value of the characteristic (Cd) above the prescription value ($Cd_{set}$) when the first inlet value ($Cd_{in1}$) is below the prescription value ($Cd_{set}$).

In a $15^{th}$ aspect according to any one of the preceding aspects, said parameter comprises one selected in the group of:
  an effective dialysance for one or more substances of the treatment unit (D),
  an effective clearance for one or more substances of the treatment unit (K),
  a concentration of a substance in blood ($Cb_{in}$) upstream the blood treatment unit,
  a dialysis dose at time (t) after start of the treatment (K·t/V).

In a $16^{th}$ aspect according to any one of the preceding aspects, the parameter comprises the effective dialysance (D).

In a $17^{th}$ aspect according to the preceding aspect, each computed value ($D_k$) of said parameter for the respective variation ($V_k$) is obtained using the formula:

$$D_k = 500 \cdot [(Cd_{in1} - Cd_{out1}) + (Cd_{in2} - Cd_{out2})]/(Cd_{in1} - Cd_{in2})$$

where:
  $Cd_{out1}$ is the first outlet value taken by the characteristic in the spent dialysate line downstream of the secondary chamber in response to the change of characteristic ($Cd_{in}$) in the preparation line to said first inlet value $Cd_{in1}$,
  $Cd_{out2}$ is the second value taken by the characteristic in the spent dialysate line downstream of the secondary chamber in response to the change of characteristic ($Cd_{in}$) in the preparation line at said second inlet value ($Cd_{in2}$),
  $Cd_{in2}$ are first and second inlet values taken by the characteristic (Cd) in the preparation line upstream of the secondary chamber.

In a $18^{th}$ aspect according to the $16^{th}$ or $17^{th}$ aspect, the parameter comprises a concentration of a substance in blood ($Cb_{in}$) upstream the blood treatment unit.

In a $19^{th}$ aspect according to the preceding aspect, each computed value ($Cb_{in(k)}$) of said parameter for the respective variation ($V_k$) is obtained using the formula:

$$Cb_{in(k)} = [(500 \cdot Cd_{out2}) - (D_k \cdot Cd_{in2})]/(500 - D_k),$$

where $D_k$ is calculated using the formula of the $17^{th}$ aspect.

In a $20^{th}$ aspect according to any one of the preceding aspects, the control unit is configured for executing a validation routine in connection to each calculated value of the parameter, the validation routine comprising the following steps:

determining from a plurality of calculated values, preferably from more than 3 values, more preferably from more than 5 values, of the parameter a trend over time of the same parameter;
   establishing when one or more of the calculated values of the parameter deviates from the determined trend;
   discarding as invalid the calculated values deviating from the determined trend.

In a 21$^{st}$ aspect according to the preceding aspect, determining said trend comprises determining an ideal curve representative of a plurality of calculated values of the parameter, and wherein establishing when one or more of the calculated values deviates from the trend comprises comparing each calculated value of the parameter with the ideal curve and verifying if the calculated value differs from values of the curve by more than a prescribed threshold.

In a 22$^{nd}$ aspect according to any one of the preceding aspects, the control unit is configured for determining calculated values of at least a first and a second parameters indicative of the effectiveness of the extracorporeal blood treatment and wherein the control unit is configured for:

determining a trend over time of a first parameter from a plurality of calculated values, preferably from more than 3 values, more preferably from more than 5 values, taken by said first parameter,
   determining a trend over time of a second parameter from a plurality of calculated values, preferably from more than 3 values, more preferably from more than 5 values, taken by said second parameter,
   establishing if the calculated values of the first and second parameters deviate from the respective determined trend in correspondence of a same time interval,
   discarding the calculated values of the first and second parameters deviating from the respective trend in correspondence of a same time interval.

In a 23$^{rd}$ aspect according to any one of the preceding aspects, wherein the control unit is configured for determining calculated values of at least a first and a second parameters indicative of the effectiveness of the extracorporeal blood treatment and wherein the control unit is configured for:

determining a trend over time of a first parameter from a plurality of calculated values, preferably from more than 3 values, more preferably from more than 5 values, taken by said first parameter,
   determining a trend over time of a second parameter from a plurality of calculated values, preferably from more than 3 values, more preferably from more than 5 values, taken by said second parameter,
   establishing if the calculated values of the first and second parameters deviate from the respective determined trend and in the affirmative:
     a) verifying whether one or both of the first and second parameters deviate from the respective trend in correspondence of a same time or time interval,
     b) whether the deviation is temporary or lasts for the rest of the treatment.
   identifying a potential cause of the deviation based on factors a) and b).

In a 24$^{th}$ aspect according to the preceding aspect, the control unit is configured to associate at least a first cause if both the first and second parameters deviate from the respective trend in correspondence of a same time or time interval, and at least a second cause different from the first cause if only one of the first and second parameters deviate from the respective trend in correspondence of a same time or time interval.

In a 25$^{th}$ aspect according to any one of the preceding three aspects, further wherein the first parameter is one of the effective dialysance (D) for at least one substance, and the effective clearance (K) for at least one substance; and the second parameter is one of the blood conductivity or the plasma conductivity upstream the blood treatment unit (2).

In a 26$^{th}$ aspect according to any one of the preceding aspects, the apparatus comprises said treatment unit, wherein:

the preparation line has one end connected to an inlet of the secondary chamber of the treatment unit,
   the spent dialysate line has one end connected to the outlet of said secondary chamber,
   a blood withdrawal line is connected at an inlet of the primary chamber and
   a blood return line is connected at an outlet of the primary chamber.

A 27$^{th}$ aspect relates to a method of controlling an apparatus for extracorporeal treatment of blood, the apparatus being of the type comprising:

a preparation line having one end configured for being connected to an inlet of a secondary chamber of a treatment unit having a primary chamber and said secondary chamber separated by a semi-permeable membrane;
   a spent dialysate line having one end configured for being connected to an outlet of said secondary chamber; the method comprising execution of the following steps:
     causing a treatment liquid to flow in the preparation line to the secondary chamber, the treatment liquid having a characteristic (Cd) which is one selected in the group of:
       conductivity of the treatment liquid,
       concentration of at least one substance in the treatment liquid;
     receiving at least one prescription value (Cd$_{set}$) for the characteristic (Cd);
     causing a plurality of consecutive and continuously repeated variations (V$_k$) of the characteristic (Cd) around the prescription value (Cd$_{set}$) in the liquid flowing in the preparation line, each one of said variations being obtained by:
       changing the value of the characteristic (Cd) in the preparation line until a first inlet value (Cd$_{in1}$) of the characteristic is reached, said first value (Cd$_{in1}$) being different from the prescription value (Cd$_{set}$),
       keeping the characteristic (Cd) in the preparation line unchanged at said first inlet value (Cd$_{in1}$) during a first time interval ($\Delta T_1$),
       changing the value of the characteristic (Cd) in the preparation line until a second inlet value (Cd$_{in2}$) of the characteristic is reached, wherein the second inlet value (Cd$_{in2}$) is different than the prescription value (Cd$_{set}$) and the prescription value (Cd$_{set}$) is comprised between said first and said second inlet values (Cd$_{in1}$; Cd$_{in2}$), keeping the characteristic (Cd) in the preparation line unchanged at said second inlet value (Cd$_{in2}$) during a second time interval ($\Delta T_2$), following (e.g. immediately following) the first time interval,
     during each of said variations (V$_k$) the characteristic (Cd) in the liquid flowing in the preparation line taking the first inlet value (Cd$_{in1}$) during the first time interval ($\Delta T_1$) and taking the second inlet value ($Cd_{in2}$) during the second time interval ($\Delta T_2$);

for of each of said variations ($V_k$):

receiving measures of a first and second outlet values ($Cd_{out1}$, $Cd_{out2}$) respectively adopted by the characteristic (Cd) in the spent dialysate line in response to the first and second inlet values ($Cd_{in1}$; $Cd_{in2}$) taken by the same characteristic in the preparation line, and computing at least one value of a parameter (D, $Cb_{in}$, K, K·t/V) indicative of the effectiveness of the extracorporeal blood treatment from said first and second outlet values ($Cd_{out1}$, $Cd_{out2}$) taken by the characteristic (Cd) in the spent dialysate line.

In a $28^{th}$ aspect according to the $27^{th}$ aspect, the first time interval ($\Delta T_1$) and the second time interval ($\Delta T_2$) of each variation ($V_k$) have same duration.

In a $29^{th}$ aspect according to any one of the preceding two aspects, the first and second inlet values ($Cd_{in1}$, $Cd_{in2}$) in each variation ($V_k$) differ from the prescribed value ($Cd_{set}$) by a same quantity.

In a $30^{th}$ aspect according to any one of the preceding three aspects, the first and second inlet values ($Cd_{in1}$, $Cd_{in2}$) in each variation ($V_k$) differ from the prescribed value ($Cd_{set}$) by a same quantity comprised between 0.3 and 1 mS/cm.

In a $31^{st}$ aspect according to any one of the preceding four aspects, the first and second inlet values ($Cd_{in1}$, $Cd_{in2}$) in each variation ($V_k$) define a sequence of variations ($V_k$) symmetrically evolving around the prescribed value.

In a $32^{nd}$ aspect according to any one of the preceding aspects from the $27^{th}$ to the $31^{st}$, said variations ($V_k$) of the characteristic (Cd) around the prescription value ($Cd_{set}$) are consecutively and continuously repeated during a significant portion of a treatment time (T) such that a plurality of values of the parameter (D, $Cb_{in}$, K, K·t/V) indicative of the effectiveness of the extracorporeal blood treatment are correspondingly determined.

In a $33^{rd}$ aspect according to the preceding aspect, said significant portion of the treatment time is at least 25% of said treatment time (T) or at least 50% of said treatment time (T) or at least 75% of said treatment time (T) or the entire treatment time (T).

In a $32^{nd}$ aspect according to any one of the preceding aspects from the $27^{th}$ to the $31^{st}$, each first time interval ($\Delta T_1$) and each second time interval ($\Delta T_2$) in each variation is longer than 2 minutes and shorter than 6 minutes.

In a $33^{rd}$ aspect according to any one of the preceding aspects from the $27^{th}$ to the $32^{nd}$, wherein changing the value of the characteristic (Cd) in the preparation line until a first inlet value ($Cd_{in1}$) of the characteristic is reached comprises a step increase or a step decrease of the characteristic, and wherein changing the value of the characteristic (Cd) in the preparation line until a second inlet value ($Cd_{in2}$) of the characteristic is reached comprises a step decrease or a step increase of the characteristic such that the consecutive and continuously repeated variations ($V_k$) define a square wave.

In a $34^{th}$ aspect according to any one of the preceding aspects from the $27^{th}$ to the $33^{rd}$, at each variation ($V_k$) said change of the value of the characteristic (Cd) until a first inlet value ($Cd_{in1}$) is reached is an increase of the value of the characteristic (Cd) above the prescription value ($Cd_{set}$) or a decrease of the value of the characteristic (Cd) below the prescription value ($Cd_{set}$).

In a $35^{th}$ aspect according to any one of the preceding aspects from the $27^{th}$ to the $34^{th}$, at each variation ($V_k$) said change of the value of the characteristic (Cd) until a second inlet value ($Cd_{in2}$) is reached is a decrease of the value of the characteristic (Cd) below the prescription value ($Cd_{set}$) when the first value ($Cd_{in1}$) is above the prescription value ($Cd_{set}$) or an increase of the value of the characteristic (Cd) above the prescription value ($Cd_{set}$) when the first inlet value ($Cd_{in1}$) is below the prescription value ($Cd_{set}$).

In a $36^{th}$ aspect according to any one of the preceding aspects from the $27^{th}$ to the $35^{th}$, said parameter comprises one selected in the group of:

an effective dialysance for one or more substances of the treatment unit (D), an effective clearance for one or more substances of the treatment unit (K), a concentration of a substance in blood ($Cb_{in}$) upstream the blood treatment unit, a dialysis dose at time (t) after start of the treatment (K·t/V).

In a $37^{th}$ aspect according to any one of the preceding aspects from the $27^{th}$ to the $36^{th}$, the parameter comprises the effective dialysance (D), each computed value ($D_k$) of said parameter for the respective variation ($V_k$) being obtained using the formula:

$$D_k = 500 \cdot [(Cd_{in1}-Cd_{out1})+(Cd_{in2}-Cd_{out2})]/(Cd_{in1}-Cd_{in2})$$

where:

$Cd_{out1}$ is the first outlet value taken by the characteristic in the spent dialysate line downstream of the secondary chamber in response to the change of characteristic ($Cd_{in}$) in the preparation line to said first inlet value $Cd_{in1}$, $Cd_{out2}$ is the second value taken by the characteristic in the spent dialysate line downstream of the secondary chamber in response to the change of characteristic ($Cd_{in}$) in the preparation line at said second inlet value ($Cd_{in2}$), $Cd_{in2}$ are first and second inlet values taken by the characteristic (Cd) in the preparation line upstream of the secondary chamber.

In a $38^{th}$ aspect according to the preceding aspect, the parameter comprises a concentration of a substance in blood ($Cb_{in}$) upstream the blood treatment unit, each computed value ($Cb_{in(k)}$) of said parameter for the respective variation ($V_k$) being obtained using the formula:

$$Cb_{in(k)} = [(500 \cdot Cd_{out2})-(D_k \cdot Cd_{in2})]/(500-D_k),$$

where $D_k$ is calculated using the formula of the $17^{th}$ aspect.

In a $39^{th}$ aspect according to any one of the preceding aspects from the $27^{th}$ to the $38^{th}$, the method comprises executing a validation routine in connection to each calculated value of the parameter, the validation routine comprising the following steps:

determining from a plurality of calculated values, preferably from more than 3 values, more preferably from more than 5 values, of the parameter a trend over time of the same parameter;

establishing when one or more of the calculated values of the parameter deviates from the determined trend;

discarding as invalid the calculated values deviating from the determined trend.

In a $40^{th}$ aspect according to the preceding aspect, determining said trend comprises determining an ideal curve representative of a plurality of calculated values of the parameter, and wherein establishing when one or more of the calculated values deviates from the trend comprises comparing each calculated value of the parameter with the ideal curve and verifying if the calculated value differs from values of the curve by more than a prescribed threshold.

In a 41$^{st}$ aspect according to any one of the preceding aspects from the 27$^{th}$ to the 40$^{th}$, the method comprises determining calculated values of at least a first and a second parameters indicative of the effectiveness of the extracorporeal blood treatment, said method further comprising the steps of:
- determining a trend over time of a first parameter from a plurality of calculated values, preferably from more than 3 values, more preferably from more than 5 values, taken by said first parameter,
- determining a trend over time of a second parameter from a plurality of calculated values, preferably from more than 3 values, more preferably from more than 5 values, taken by said second parameter,
- establishing if the calculated values of the first and second parameters deviate from the respective determined trend in correspondence of a same time interval,
- discarding the calculated values of the first and second parameters deviating from the respective trend in correspondence of a same time interval.

In a 42$^{nd}$ aspect according to any one of the preceding aspects from the 27$^{th}$ to the 41$^{st}$, the method comprises determining calculated values of at least a first and a second parameters indicative of the effectiveness of the extracorporeal blood treatment, said method further comprising the steps of:
- determining a trend over time of a first parameter from a plurality of calculated values, preferably from more than 3 values, more preferably from more than 5 values, taken by said first parameter,
- determining a trend over time of a second parameter from a plurality of calculated values, preferably from more than 3 values, more preferably from more than 5 values, taken by said second parameter,
- establishing if the calculated values of the first and second parameters deviate from the respective determined trend and in the affirmative:
  a) verifying whether one or both of the first and second parameters deviate from the respective trend in correspondence of a same time or time interval,
  b) whether the deviation is temporary or lasts for the rest of the treatment.
- identifying a potential cause of the deviation based on factors a) and b).

In a 43$^{rd}$ aspect according to the preceding aspect, the method provides for associating at least a first cause if both the first and second parameters deviate from the respective trend in correspondence of a same time or time interval, and at least a second cause different from the first cause if only one of the first and second parameters deviate from the respective trend in correspondence of a same time or time interval.

In a 44$^{th}$ aspect according to any one of the preceding three aspects, further wherein the first parameter is one of the effective dialysance (D) for at least one substance, and the effective clearance (K) for at least one substance; and the second parameter is one of the blood conductivity or the plasma conductivity upstream the blood treatment unit (2).

In a 45$^{th}$ aspect according to any one of the preceding aspects from the 27$^{th}$ to the 44$^{th}$, the step of causing a plurality of consecutive and continuously repeated variations ($V_k$) of the characteristic (Cd) around the prescription value (Cd) is configured such that, taking as base line the line defined over time by the prescribed value (Cd$_{set}$), the sum of the areas ($A_k$) formed between said base line and the portions of curve representative of the inlet conductivity/concentration positioned above the base line is identical or close to the sum of the areas ($B_k$) defined between the base line and the portions of curve representative of the inlet conductivity/concentration curve positioned below the base line. This allows the respect of the prescription value (Cd$_{set}$) across the treatment irrespective of the continuous conductivity/concentration variations imposed to the inlet conductivity.

In a 46$^{th}$ aspect according to any one of the preceding aspects from the 27$^{th}$ to the 45$^{th}$, the method is executed by a control unit which is part of said apparatus for extracorporeal treatment of blood.

In a 47$^{th}$ aspect a data carrier including instructions executable by a control unit of a blood treatment (for instance of the blood treatment apparatus of any one of aspects from 1$^{st}$ to 26$^{th}$ apparatus or the blood treatment apparatus indicated in the 46$^{th}$ aspect) is provided. The instructions are configured such that, when executed by the control unit, they cause execution of the method according to any one of the preceding aspects from 27$^{th}$ to 46$^{th}$.

In a 47$^{th}$ aspect according to the preceding aspect the data carrier may be any support suitable for storing data, such as by way of non-limiting example: a RAM, a ROM, an EPROM, an optical or a magnetic disc, an electromagnetic wave, a mass memory storage device such as an Hard Disk or a flash memory bank.

DESCRIPTION OF THE DRAWINGS

Aspects of the invention are shown in the attached drawings, which are provided by way of non-limiting example, wherein:

FIGS. 2A, 2B, 2C conductivity (or concentration) vs. time diagram showing the conductivity profile in the fresh dialysate line, according to alternative aspects of the invention;

DETAILED DESCRIPTION

Figure 7:
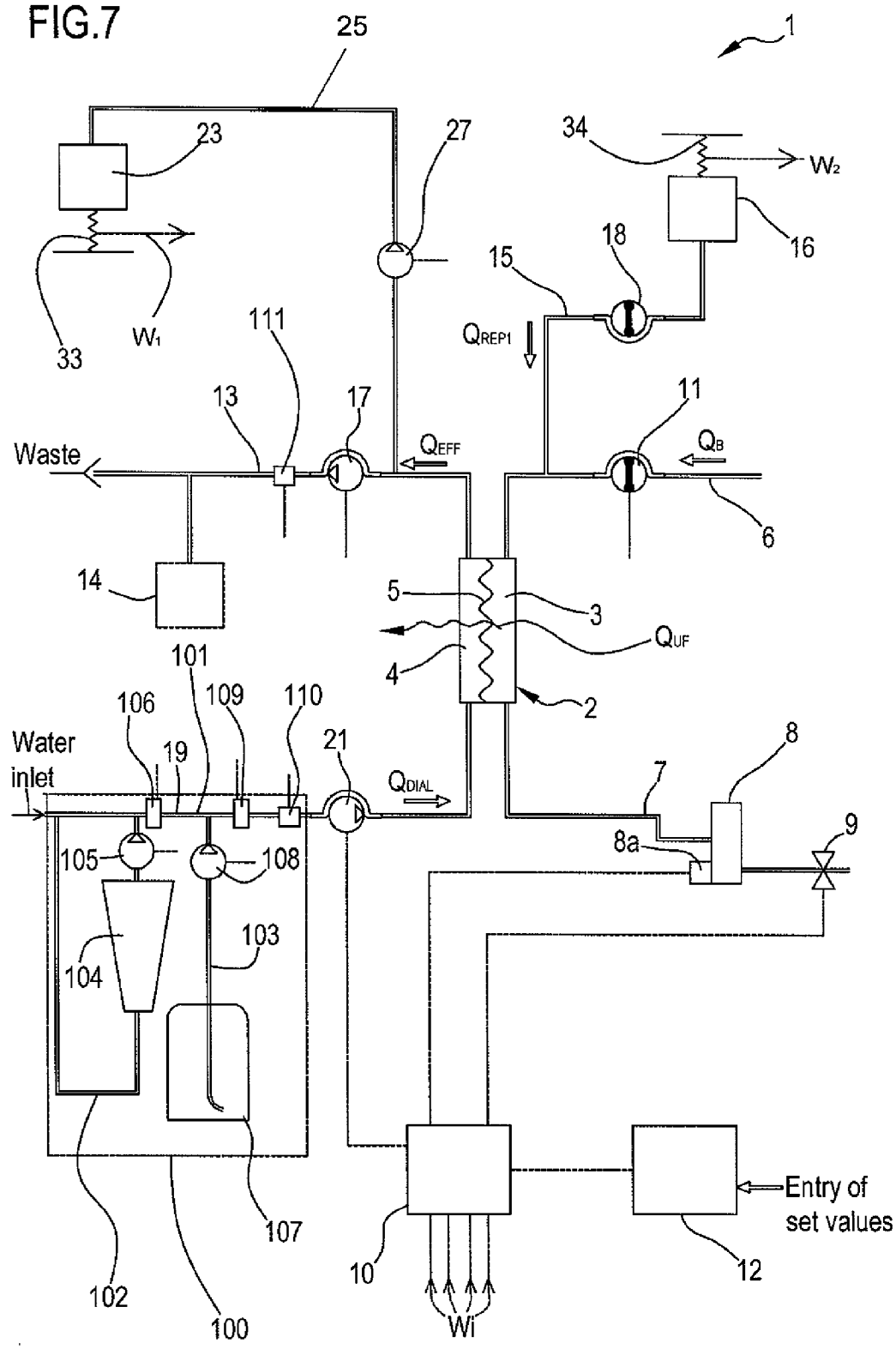
FIG. 7 shows a schematic diagram of a blood treatment apparatus according to one aspect of the invention.
Figure 8:
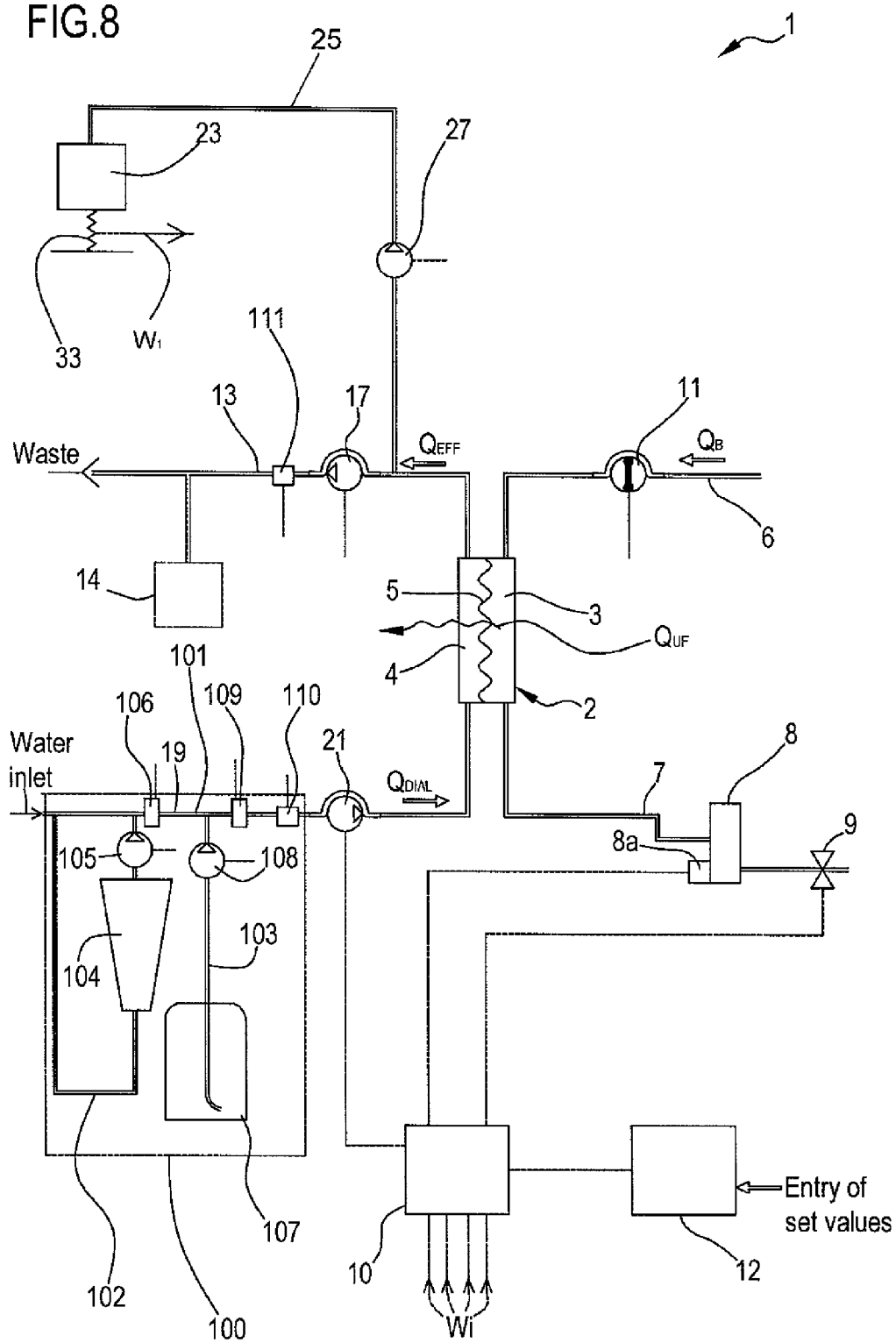
FIG. 8 shows a schematic diagram of an alternative embodiment of a blood treatment apparatus according to another aspect of the invention.

Non-limiting embodiments of an apparatus 1 for extracorporeal treatment of blood—which may implement innovative aspects of the invention—are shown in FIGS. 7 and 8. The apparatus 1 may be configured to determine a parameter indicative of the effectiveness of the treatment delivered to a patient (here below also referred to as 'effectiveness parameter'). In below description and in FIGS. 7 and 8 same components are identified by same reference numerals.

FIG. 7 shows an apparatus 1 configured to deliver any one of treatments like ultrafiltration, hemodialysis and hemodiafiltration, while FIG. 8 shows an apparatus configured to deliver hemodialysis or ultrafiltration treatments.

The apparatus 1 comprises a treatment unit 2 (such as an hemofilter, an ultrafilter, an hemodiafilter, a dialyzer, a plasmafilter and the like) having a primary chamber 3 and a secondary chamber 4 separated by a semi-permeable membrane 5; depending upon the treatment, the membrane of the filtration unit may be selected to have different properties and performances.

A blood withdrawal line 6 is connected to an inlet of the primary chamber 3, and a blood return line 7 is connected to an outlet of the primary chamber 3. In use, the blood withdrawal line 6 and the blood return line 7 are connected to a needle or to a catheter or other access device (not shown) which is then placed in fluid communication with the patient vascular system, such that blood may be withdrawn through the blood withdrawal line, flown through the primary chamber and then returned to the patient's vascular system through the blood return line. An air separator, such as a bubble trap 8 may be present on the blood return line; moreover, a safety clamp 9 controlled by a control unit 10 may be present on the blood return line downstream the bubble trap 8. A bubble sensor 8a, for instance associated to the bubble trap 8 or coupled to a portion of the line 7 between bubble trap 8 and clamp 9 may be present: if present, the bubble sensor is connected to the control unit 10 and sends to the control unit signals for the control unit to cause closure of the clamp 9 in case one or more bubbles above certain safety thresholds are detected. As shown in FIG. 7, the blood flow through the blood lines is controlled by a blood pump 11, for instance a peristaltic blood pump, acting either on the blood withdrawal line (as shown in FIG. 7) or on the blood return line. An operator may enter a set value for the blood flow rate $Q_B$ through a user interface 12 and the control unit 10, during treatment, is configured to control the blood pump based on the set blood flow rate. The control unit may comprise a digital processor (CPU) and a memory (or memories), an analogical type circuit, or a combination thereof as explained in greater detail in below section dedicated to the 'control unit'.

An effluent fluid line or spent dialysate line 13 is connected, at one end, to an outlet of the secondary chamber 4 and, at its other end, to a waste which may be a discharge conduit or an effluent fluid container 14 (dashed lines in FIGS. 7 and 8) collecting the fluid extracted from the secondary chamber. An effluent fluid pump 17 operates on the effluent fluid line under the control of control unit 10 to regulate the flow rate $Q_{eff}$ across the effluent fluid line. The apparatus may also include an ultrafiltration line 25 branching off the effluent line 13 and provided with a respective ultrafiltration pump 27 also controlled by control unit 10. The embodiment of FIG. 7 presents a pre-dilution fluid line 15 connected to the blood withdrawal line: this line 15 supplies replacement fluid from an infusion fluid container 16 connected at one end of the pre-dilution fluid line. Although in FIG. 7 a container 16 is shown as the source of infusion fluid, this should not be interpreted in a limitative manner: indeed, the infusion fluid may also come from an on line preparation section 100 part of the apparatus 1. Note that alternatively to the pre-dilution fluid line the apparatus of FIG. 1 may include a post-dilution fluid line (not shown in FIG. 7) connecting an infusion fluid container to the blood return line. Finally, as a further alternative (not shown in FIG. 7) the apparatus of FIG. 1 may include both a pre-dilution and a post infusion fluid line: in this case each infusion fluid line may be connected to a respective infusion fluid container or the two infusion fluid lines may receive infusion fluid from a same source of infusion fluid such as a same infusion fluid container. Once again, the source of infusion fluid may also be an online preparation section part of the apparatus 1 (similar to the device 100 described herein below) supplying fluid to the post and/or pre dilution lines. Furthermore, an infusion pump 18 operates on the infusion line 15 to regulate the flow rate $Q_{rep}$ through the infusion line. Note that in case of two infusion lines (pre-dilution and post-dilution) each infusion line may be provided with a respective infusion pump.

Figure 1:
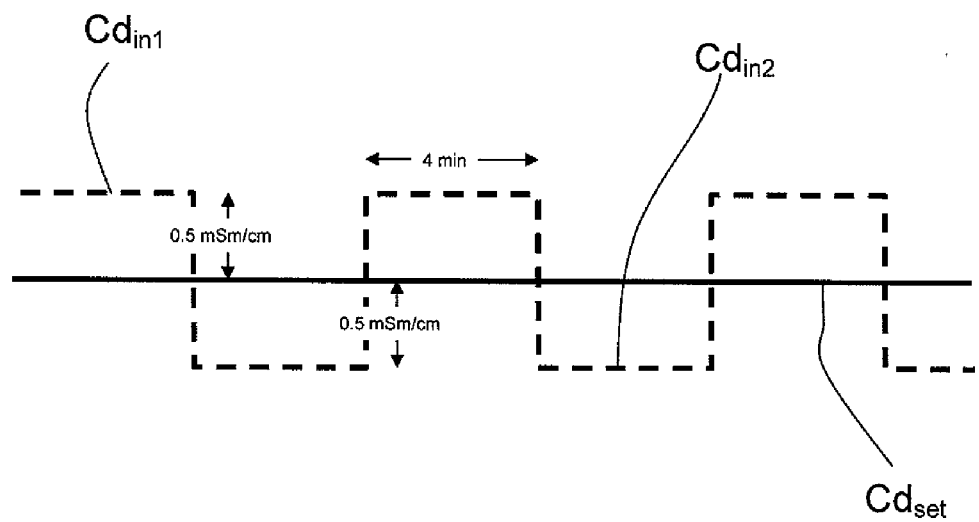
FIG. 1 shows a conductivity (or concentration) vs. time diagram showing the conductivity profile in the fresh dialysate line, according to an aspect of the invention.

The apparatus of FIG. 1, further includes a fluid preparation line, such as dialysis fluid line 19 connected at one end with a water inlet and at its other end with the inlet of the secondary chamber 4 of the filtration unit for supplying fresh dialysis liquid to the secondary chamber 4. A dialysis fluid pump 21 works on the dialysis liquid fluid line under the control of said control unit 10, to supply fluid from the dialysis liquid container to the secondary chamber at a flow rate $Q_{dial}$. The dialysis fluid pump 21, the ultrafiltration pump 27, the concentrate pumps 105 and 108, the infusion fluid pump 15 and the effluent fluid pump 17 are operatively connected to the control unit 10 which controls the pumps as it will be in detail disclosed herein below. The line 19 links the haemodialyser or hemodiafilter 2 to a device 100 for preparing the dialysis liquid, comprising a main line 101, the upstream end of which is designed to be connected to a supply of running water. Connected to this main line 101 are a first secondary line 102 and a second secondary line 103. The first secondary line 102, which may be looped back onto the main line 101, is provided with a connector configured for fitting a container 104, such as a bag or cartridge or other container, containing sodium bicarbonate in granule form (alternatively a concentrate in liquid form may be used). Line 102 is furthermore equipped with a concentrate pump 105 for metering the sodium bicarbonate into the dialysis liquid: as shown in FIG. 7 the pump may be located downstream of the container 104. The operation of the pump 105 is determined by the comparison between 1) a conductivity set point value for the solution forming at the junction of the main line 101 and the first secondary line 102 and 2) the value of the conductivity of this mixture measured by means of a first conductivity probe 106 located in the main line 101 immediately downstream of the junction between the main line 101 and the first secondary line 102. The free end of the second secondary line 103 is intended to be immersed in a container 107 for a concentrated saline solution, e.g. containing sodium chloride, calcium chloride, magnesium chloride and potassium chloride, as well as acetic acid. The second secondary line 103 is equipped with a pump 108 for metering sodium into the dialysis liquid, the operation of which pump depends on the comparison between 1) a second conductivity setpoint value for the solution forming at the junction of the main line 101 and the second secondary line 103 and 2) the value of the conductivity of this solution measured by means of a second conductivity probe 109 located in the main line 12 immediately downstream of the junction between the main line 12 and the secondary line 103. Note that as an alternative, instead of conductivity sensors concentration sensors may in principle be used. Moreover, the specific nature of the concentrates contained in containers 104 and 107 may be varied depending upon the circumstances and of the type of dialysis fluid to be prepared.

The control unit 10 is also connected to the user interface 12, for instance a graphic user interface, which receives operator's inputs and displays the apparatus outputs. For instance, the graphic user interface 12 may include a touch screen, a display screen and hard keys for entering user's inputs or a combination thereof.

The embodiment of FIG. 8 shows an alternative apparatus 1 designed for delivering any one of treatments like hemodialysis and ultrafiltration. In the apparatus shown in FIG. 8 the same components described for the embodiment of FIG. 7 are identified by same reference numerals and thus not described again. In practice, differently from the hemodiafiltration apparatus of FIG. 7, the apparatus of FIG. 8 does not present any infusion line.

In each one of the above described embodiments, flow sensors 110, 111 (either of the volumetric or of the mass type) may be used to measure flow rate in each of the lines. Flow sensors are connected to the control unit 10. In the example of FIG. 7 where the infusion line 15 and the ultrafiltration line 25 lead to a respective bag 16, 23, scales may be used to detect the amount of fluid delivered or collected. For instance, the apparatus of FIG. 7 includes a first scale 33 operative for providing weight information $W_1$ relative to the amount of the fluid collected in the ultrafiltration container 23 and a second scale 34 operative for providing weight information $W_2$ relative to the amount of the fluid supplied from infusion container 16. In the embodiment of FIG. 8, the apparatus includes a first scale 33 operative for providing weight information W, relative to the amount of the fluid collected in the ultrafiltration container 23. The scales are all connected to the control unit 10 and provide said weight information $W_i$ for the control unit to determine the actual quantity of fluid in each container as well as the actual flow rate of fluid supplied by or received in each container.

In the example of FIGS. 7 and 8, in order to control the fluid balance between the quantity of fluid supplied to the secondary chamber 4 and the quantity of fluid extracted from the secondary chamber, the flow-meters 110, 111 positioned on the fresh dialysate line and on the waste line 13 provide the control unit 10 with signals indicative of the flow of fluid through the respective lines and the scale or scales provide weight information which allow the control unit to derive the flow rate through the ultrafiltration line 25 and, if present, through the infusion line 15. The control unit is configured to control at least pumps 17, 21 and 27 (in case of FIG. 7 also pump 18) to make sure that a prefixed patient fluid removal is achieved in the course of a treatment time T, as required by the prescription provided to the control unit, e.g. via user interface 12. Note that other fluid balance systems may be used: for instance in case the apparatus includes a container as source of fresh dialysis fluid and a container to collect waste, then scales may be used to detect the amount of fluid delivered or collected by each container and then inform the control unit accordingly. As a further alternative, systems based on volumetric control may be used where the fresh dialysis liquid line 19 and the waste line 13 are connected to a balance chamber system assuring that—at each instant—the quantity of liquid flowing into line 19 is identical to the quantity of fluid exiting from line 13.

From a structural point of view one or more, containers 104, 107, 16, 23 may be disposable plastic containers. The blood lines 6, 7 lines and the filtration unit may also be plastic disposable components which may be mounted at the beginning of the treatment session and then disposed of at the end of the treatment session. Pumps, e.g. peristaltic pumps or positive displacement pumps, have been described as means for regulating fluid flow through each of the lines; however, it should be noted that other flow regulating means may alternatively be adopted such as for example valves or combinations of valves and pumps. The scales may comprise piezoelectric sensors, or strain gauges, or spring sensors, or any other type of transducer able to sense forces applied thereon. As already explained, the conductivity sensors may be replaced by concentration sensors.

Operation

Figure 9:
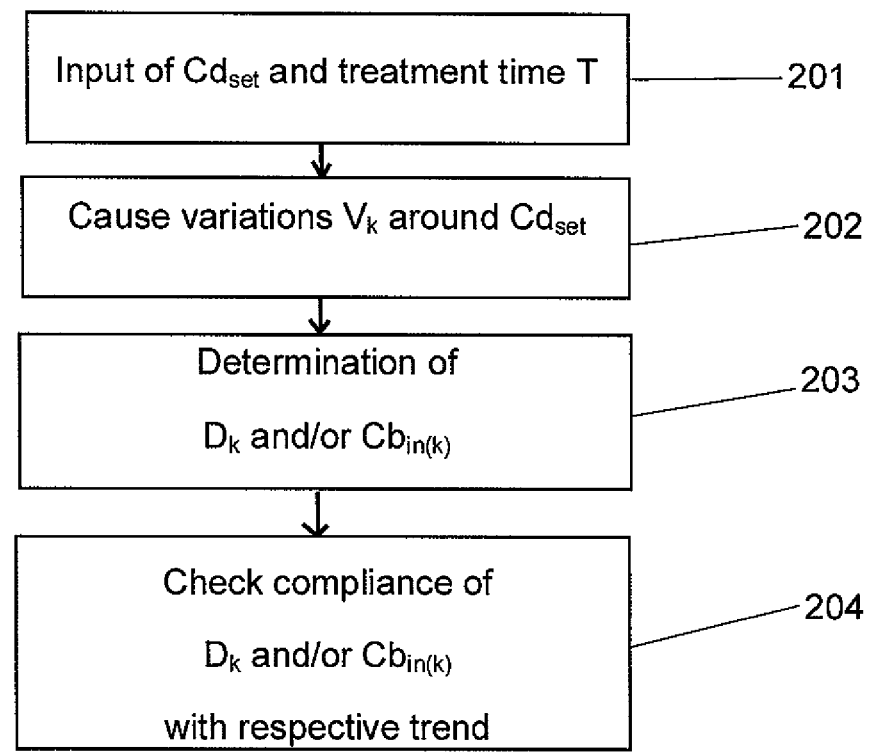
FIG. 9 is a schematic flowchart of a method according to one aspect of the invention.

The operation of the above apparatus for measuring a parameter indicative of the effectiveness of the blood treatment is now described, with reference to the attached figures and to the flowchart of FIG. 9 in particular.

The control unit 10 is configured for commanding the pumps 105, 108 and 21 and for causing the preparation of a treatment liquid in section 100 and the flow of the treatment liquid in the main line 101, in line 19 and into the secondary chamber. The control unit may receive, e.g. via user interface 12, at least one prescription value $Cd_{set}$ for a characteristic Cd of the treatment liquid which should be kept during the treatment (step 201). The characteristic Cd may be the conductivity of the treatment liquid, or the concentration of at least one substance (e.g. sodium or other electrolytes) in the treatment liquid. Note that the prescription value may be constant or it may vary according to a prefixed profile during the treatment. The control unit is also configured to cause, either upon receipt of a user command or automatically upon treatment start, a plurality of consecutive and continuously repeated variations $V_k$ of the characteristic Cd around the prescription value $Cd_{set}$ in the liquid flowing in the preparation line (step 202); the variations define for instance a square wave around the prescription value, as shown in FIG. 1 where the straight continuous line represent the constant prescription value for the characteristic, while the dashed line represents the alternated profile imposed by the control unit to the characteristic real value. For instance, the up and down variation in the value of the characteristic Cd may have the shape of a step increase or a step such that the consecutive and continuously repeated variations $V_k$ define a square wave showing an almost instantaneous increase (or respectively decrease) of the characteristic value at each change in the value of the characteristic.

Figure 2:
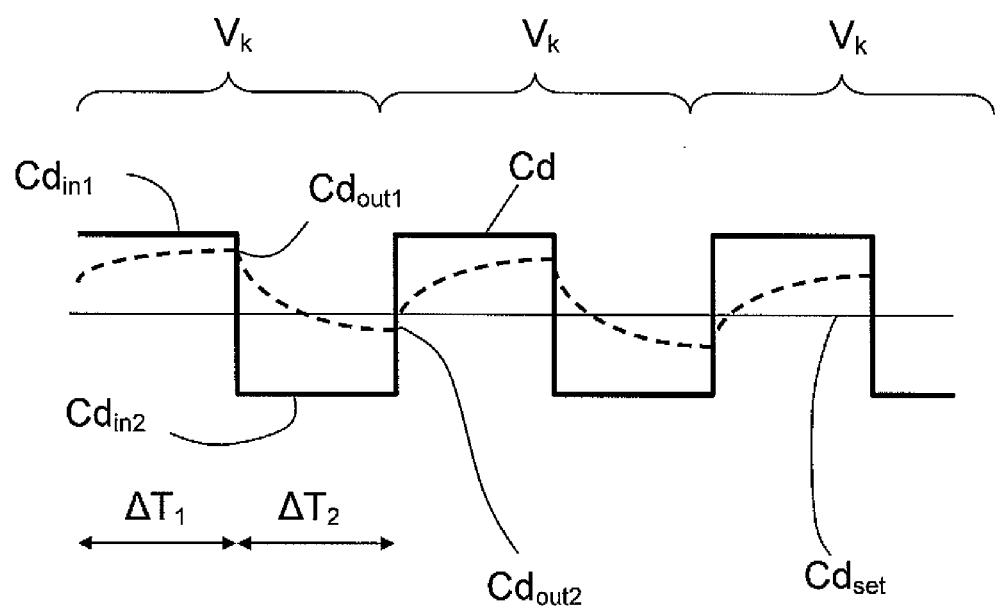
FIG. 2 shows a conductivity (or concentration) vs. time diagram showing the conductivity profile in the fresh and in the spent dialysate line, according to another aspect of the invention.

The control unit 10 is configured to impose the variations by changing the speed of pump 105 under the control of the conductivity sensor 106. More in detail, the control unit is configured to perform the following steps:

change the value of the characteristic Cd in the preparation line until a first inlet value $Cd_{in1}$ of the characteristic is reached; as may be seen in FIGS. 1 and 2, the first value $Cd_{in1}$ is different from the prescription value $Cd_{set}$;

keep the characteristic Cd in the preparation line unchanged at said first inlet value $Cd_{in1}$ during a first time interval $\Delta T_1$; in other words, the conductivity or concentration is left constant for a while;

change the value of the characteristic Cd in the preparation line until a second inlet value $Cd_{in2}$ of the characteristic is reached; as may be seen in FIGS. 1 and 2, the second inlet value $Cd_{in2}$ is different than the prescription value $Cd_{set}$; moreover, the prescription value $Cd_{set}$ is comprised between the first and second inlet values $Cd_{in1}$ and $Cd_{in2}$;

keep the characteristic Cd in the preparation line unchanged at said second inlet value $Cd_{in2}$ during a second time interval $\Delta T_2$ immediately following the first time interval.

The above up and down changes of the characteristic around the set prescription value are continuously repeated defining a plurality of variations. During each of said variations $V_k$ the characteristic Cd in the liquid flowing in the preparation line takes the first inlet value $Cd_{in1}$ during the first time interval $\Delta T_1$ and takes the second inlet value $Cd_{in2}$ during the second time interval $\Delta T_2$.

Immediately after and in correspondence of each of said variations $V_k$ the control unit is configured to receive measures of a first and second outlet values $Cd_{out1}$, $Cd_{out2}$ respectively adopted by the characteristic Cd in the spent dialysate line in response to the first and second inlet values $Cd_{in1}$ and $Cd_{in2}$ taken by the same characteristic in the preparation line, and to then compute (step 203) at least one value of a parameter (such as dialysance D, blood or plasma conductivity $Cb_{in}$, clearance K, dialysis dose K·t/V) indicative of the effectiveness of the extracorporeal blood treatment. The value of the effectiveness parameter is calculated at least from said first and second outlet values $Cd_{out1}$, $Cd_{out2}$ taken by the characteristic Cd in the spent dialysate line and optionally also as a function of the first and second inlet values (note that in place of the inlet values set values may be used).

FIG. 2 shows, with continuous tract, the inlet value of the characteristic (i.e. conductivity or concentration in the preparation line) and, with dashed line, the value of the characteristic in the spent dialysate line (i.e. the outlet conductivity or concentration). Although this does not appear in the schematic drawing of FIG. 2, it should be noted that the curve representative of the outlet conductivity or concentration is timely delayed with respect to the curve representative of the inlet conductivity or concentration. Also, note that—although the curve representative of the inlet conductivity or concentration is represented as instantaneously increasing/decreasing to/from the values $Cd_{in1}$, $Cd_{in2}$—it should be noted that said increases/decreases may alternatively be in the shape of a linear or curved ramp.

In the examples shown in the appended FIGS. 1 and 2, the first time interval $\Delta T_1$ and the second time interval $\Delta T_2$ of each variation $V_k$ are shown to have same duration; furthermore, the first and second inlet values $Cd_{in1}$, $Cd_{in2}$ in each variation $V_k$ differ from the prescribed value $Cd_{set}$ by a same quantity so that the curve representative of the characteristic at the inlet of the treatment unit 1 is perfectly symmetric around its average value which is coincident with the set prescription value $Cd_{set}$ for conductivity or concentration in the fresh dialysis liquid.

In a variant shown in FIG. 2A, the duration of the first time interval $\Delta T_1$ and that of the second time interval $\Delta T_2$ of each variation $V_k$ are not the same; the first and second inlet values $Cd_{in1}$, $Cd_{in2}$ in each variation $V_k$ differ from the prescribed value $Cd_{set}$ by a same quantity.

In a further variant shown in FIG. 2B, the duration of the first time interval $\Delta T_1$ and that of the second time interval $\Delta T_2$ of each variation $V_k$ are the same; moreover, the first and second inlet values $Cd_{in1}$, $Cd_{in2}$ in each variation $V_k$ differ from the prescribed value $Cd_{set}$ by respective different quantities "a", "b". In the example of FIG. 2C, the duration of the first time interval $\Delta T_1$ and of the second time interval $\Delta T_2$ of each variation $V_k$ are not the same, and the first and second inlet values $Cd_{in1}$, $Cd_{in2}$ in each variation $V_k$ differ from the prescribed value $Cd_{set}$ by respective and different quantities "c", "d".

It may be possible, to have $Cd_{in1}$, $Cd_{in2}$, $\Delta T_1$, $\Delta T_2$ evolving across time as shown in FIGS. 2A, 2B and 2C in order not to affect (or to minimally affect) delivery of the desired prescription. In the mentioned examples, taking as base line the prescribed value $Cd_{set}$—it may be noticed that the sum of the areas $A_k$ formed between the base line and the portions of curve representative of the inlet conductivity/concentration positioned above the base line is identical or close to the sum of the areas $B_k$ defined between the base line and the portions of curve representative of the inlet conductivity/concentration curve positioned below the base line (which, once again, may be e.g. a straight line or a curve).

Furthermore, note that the control of the inlet conductivity/concentration as per above examples of FIGS. 1-2, 2A, 2B, 2C may apply even if the prescription value (base line) is not constant but is set to follow a prescription profile (e.g. a curve or a non horizontal straight line). In other words, the alternated characteristic may be designed to be perfectly equivalent from the point of view of the prescription delivered to the patient to the set prescription value (or profile if there is a set prescription changing over time $Cd_{set(t)}$.

It should also be noted that although the inlet conductivity follows a prescribed profile which is pre-stored in the memory associated to the control unit 10, it may also be possible to allow the operator to enter such profile via the user interface or to have the changes in conductivity triggered by specific events (e.g. reaching of certain values of conductivity at the outlet).

According to an example, the characteristic is the conductivity of the dialysis liquid and the first and second inlet values $Cd_{in1}$, $Cd_{in2}$ in each variation $V_k$ differ from the prescribed value $Cd_{set}$ by a same quantity comprised between 0.3 and 1 mS/cm, and define a sequence of variations $V_k$ symmetrically evolving around the prescribed value. The prescribed value may be constant and equal to a value comprised between 14.2 and 14.4 mS/cm. The alternated variation of the conductivity has average value equal to $Cd_{set}$ and therefore is equivalent, in terms of delivered treatment, to the constant prescribed value.

According to another example, the characteristic is the concentration of one substance in the fresh dialysis liquid (for instance the concentration of sodium) or the concentration of a group of substances (for instance the global concentration of a set of electrolytes). Also in this case, the first and second inlet values $Cd_{in1}$, $Cd_{in2}$ in each variation $V_k$ may differ from the prescribed value $Cd_{set}$ by a same quantity and define a sequence of variations $V_k$ symmetrically evolving around the prescribed value, which may be constant. The alternated variation of the concentration has average value equal to $Cd_{set}$ and therefore is equivalent, in terms of delivered treatment, to the constant prescribed value.

As shown in the drawings the consecutive variations $V_k$ are generated one immediately after the other such that the characteristic Cd defines a plurality of immediately continuously and repeated variations $V_k$ of the characteristic Cd around the prescription value $Cd_{set}$ in the liquid flowing in the preparation line.

According to a further aspect of the invention, the control unit may be configured for receiving a total treatment time T (see again step 201), and for consecutively and continuously repeating the variations $V_k$ of the characteristic Cd around the prescription value $Cd_{set}$ during a significant portion of the treatment time T such that a plurality of consecutive values of the parameter (D, $Cb_{in}$, K, K·t/V) indicative of the effectiveness of the extracorporeal blood treatment are correspondingly determined. In practice, the variations may be repeated during at least 50% of said treatment time T, or during at least 75% of said treatment time T or even during the entire treatment time T, without impairing on the prescription delivered and contemporaneously allowing the determination of numerous values of the parameter indicative of the effectiveness of the extracorporeal blood treatment. More in detail, each first time interval $\Delta T_1$ and each second time interval $\Delta T_2$ in each variation may be set to be longer than 2 minutes and shorter than 6 minutes. Thus, assuming for instance:

a treatment time T of 4 hours,
first time interval $\Delta T_1$=second time interval $\Delta T_2$=4 mins
repetition of the variations applied during 100% of the treatment time, would lead to the possibility of calculating 60 values of said effectiveness parameter.

In the case where the parameter is the effective dialysance D, each computed value $D_k$ of the parameter may be calculated at each the respective variation $V_k$ using the formula:

$$D_k=500\cdot[(Cd_{in1}-Cd_{out1})+(Cd_{in2}-Cd_{out2})]/(Cd_{in1}-Cd_{in2}) \quad (1)$$

where:

$Cd_{out1}$ is the first outlet value taken by the characteristic in the spent dialysate line downstream of the secondary chamber in response to the change of characteristic $Cd_{in}$ in the preparation line to said first inlet value $Cd_{in1}$; for instance the first outlet value may be a conductivity value measured by sensor 110;

$Cd_{out2}$ is the second value taken by the characteristic in the spent dialysate line downstream of the secondary chamber in response to the change of characteristic $Cd_{in}$ in the preparation line at said second inlet value $Cd_{in2}$; for instance the first outlet value may be a conductivity value measured by sensor 110;

In general $Cd_{out1}$ and $Cd_{out2}$ are both measured values of concentration or conductivity measured by sensor 110, which may be either a conductivity or a concentration sensor.

$Cd_{in1}$, $Cd_{in2}$ are first and second inlet values taken by the characteristic (Cd) in the preparation line upstream of the secondary chamber. These two values may be set values or measured values.

In the case where the parameter is the concentration of a substance in blood $Cb_{in}$ (for instance the sodium concentration in the blood upstream the blood treatment unit) each computed value $Cb_{in(k)}$ of said parameter for the respective variation $V_k$ may obtained using the formula:

$$Cb_{in(k)}=[(500\cdot Cd_{out2})-(D_k\cdot Cd_{in2})]/(500-D_k) \quad (2)$$

where $D_k$ is calculated using the formula (1).

As the apparatus 1 is operable to determine a relevant number of values of the effectiveness parameter (i.e. more than 5 and optionally more than 10) the control unit may also be configured for executing a validation routine (step 204) in connection to each calculated value of the parameter, in order to establish if each calculated is acceptable in view of the trend of the effectiveness parameter in the course of time. The validation routine comprising the following steps:

determining from a plurality of calculated values, preferably from more than 5 values, of the parameter a trend over time of the same parameter;
establishing when one (or more) of the calculated values of the parameter deviates from the determined trend;
discard as invalid the calculated values deviating from the determined trend.

Determining said trend may comprise determining an ideal curve representative of a plurality of calculated values of the parameter: this may be done with various mathematical methods; for instance the method of the least squares may be adopted to determine an ideal curve which best fits a number (such as 5 or 10 or 15) of calculated values of the effectiveness parameter. Then, the control unit may compare each calculated value of the effectiveness parameter to the ideal curve and establish when one or more of the calculated values deviates from the ideal curve. This may be done by verifying if each calculated value differs from values taken by the curve by more than a prescribed threshold. Alternatively, the control unit may compare a calculated value of the parameter at an instant (i) with values of the same parameter calculated at preceding instants (i; i–1; i–2; . . . ; i–n): if the value calculated at a certain instant is too different from the calculated values relating to preceding instants then the value at instant (i) is discarded.

Finally, according to a further aspect, the control unit may be configured to calculate two (or more) effectiveness parameters (step 203): namely, the effective dialysance D and the concentration of a substance (e.g. sodium) in the blood $Cb_{in}$ flowing upstream the blood treatment unit. In this case, the control unit may be configured for running a validation routine comprising (step 204):

determining from a plurality of calculated values, preferably from more than 5 values, of the effective dialysance a trend over time of the effective dialysance;
determining from a plurality of calculated values, preferably from more than 5 values, of the concentration of a substance in blood a trend over time of said concentration in blood;
establishing when one or more of the calculated values of the effective dialysance and of the concentration in blood deviates from the respective determined trend;
identifying if both the calculated values of effective dialysance and of the concentration in blood deviate from the respective trend in correspondence of a same time or time interval;
discarding calculated values of the effective dialysance and of the concentration in blood deviating from the respective trend in correspondence of a same time or time interval.

More in general, the control unit may be configured to identifying a potential cause of the deviation based on:

a) whether one or both of the effective dialysance and of the concentration in blood deviate from the respective trend in correspondence of a same time or time interval,
b) whether the deviation is temporary or lasts for the rest of the treatment.

Figure 3:
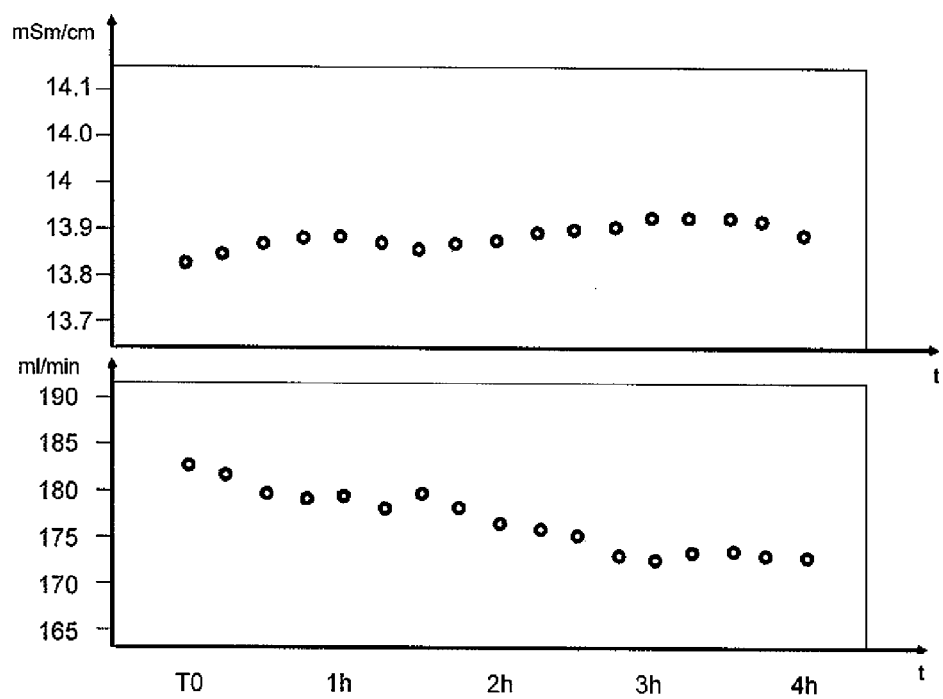
FIGS. 3-6 show diagrams representative of the plasma conductivity (expressed in mSm/cm) vs. time (expressed in hours) and of the effective ionic dialysance (expressed in ml/min) vs. time (expressed in hours); in each figure the diagram concerning plasma conductivity is placed above the diagram concerning ionic dialysance.

FIG. 3 shows a situation where both dialysance and plasma conductivity follow respective quite regular paths. In this situation, the control unit would deem the dialysance and plasma conductivity values taken over time are all acceptable and that no particular events have occurred.

Figure 4:
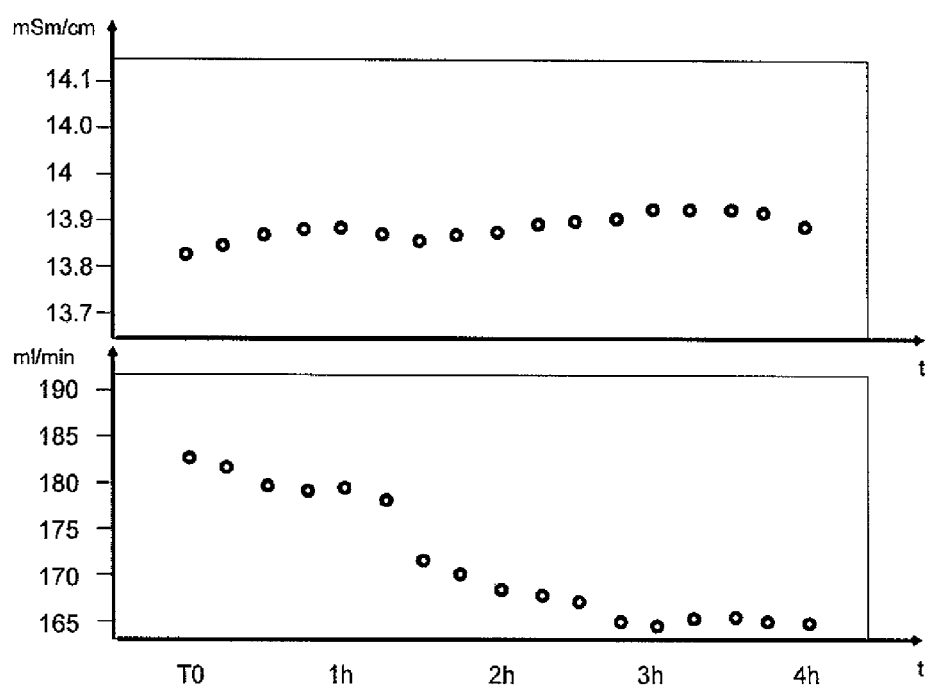

For instance if, as in FIG. 4, there is a sudden drop of dialysance while plasma conductivity remains substantially stable, it may be concluded (e.g. by the control unit) that the efficiency of the filter dropped due for instance to coagulation of blood.

Figure 5:
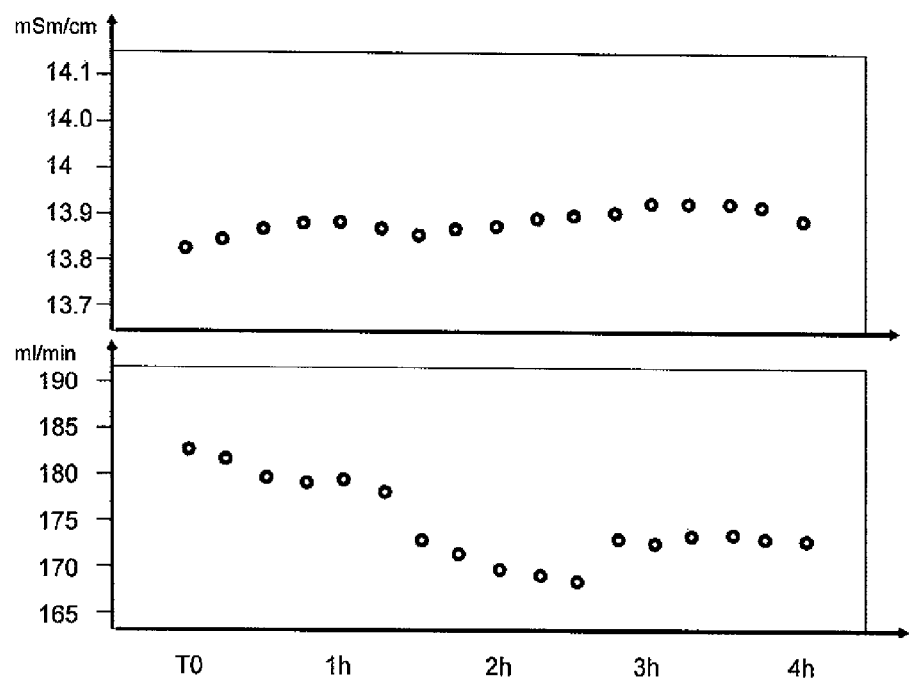

On the other hand if, as in FIG. 5, there is a drop of dialysance lasting for a limited time only (e.g. about 1 h—see the five calculated values in the middle of the dialysance curve in FIG. 5), while plasma conductivity remains substantially stable, it may be concluded (e.g. by the control unit) that the cause is linked to a change of a flow rate setting (e.g. blood pump flow rate reduced by the operator).

Figure 6:
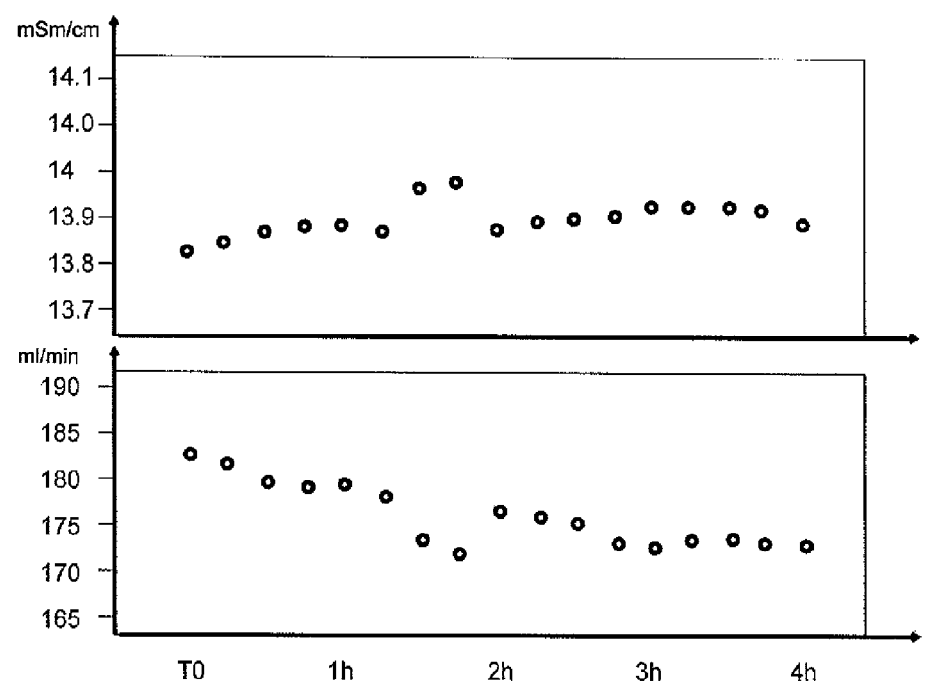

Finally if, as in FIG. 6, there is a sudden drop of dialysance while at the same time plasma conductivity undergoes a sudden increase, it may be concluded (e.g. by the control unit) that there has been an error in the determination of the effectiveness parameters and therefore the corresponding calculated values shall be discarded.

Thus, the apparatus according to this aspect of the invention may be used to discard values which for some reason do not represent realistic measures of dialysance and also to understand if certain problems or setting changes may have occurred during treatment.

Control Unit

As already indicated the apparatus according to the invention makes use of at least one control unit. This control unit may comprise a digital processor (CPU) with memory (or memories), an analogical type circuit, or a combination of one or more digital processing units with one or more analogical processing circuits. In the present description and in the claims it is indicated that the control unit is "configured" or "programmed" to execute certain steps: this may be achieved in practice by any means which allow configuring or programming the control unit. For instance, in case of a control unit comprising one or more CPUs, one or more programs are stored in an appropriate memory: the program or programs containing instructions which, when executed by the control unit, cause the control unit to execute the steps described and/or claimed in connection with the control unit. Alternatively, if the control unit is of an analogical type, then the circuitry of the control unit is designed to include circuitry configured, in use, to process electric signals such as to execute the control unit steps herein disclosed.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and the scope of the appended claims.

The invention claimed is:

1. An apparatus for extracorporeal treatment of blood comprising:
    a preparation line having one end configured for being connected to an inlet of a secondary chamber of a treatment unit having a primary chamber and said secondary chamber separated by a semi-permeable membrane;
    a spent dialysate line having one end configured for being connected to an outlet of said secondary chamber;
    a control unit configured for commanding execution of the following steps:
        causing a treatment liquid to flow in the preparation line to the secondary chamber, the treatment liquid having a characteristic which is one selected in the group of:
        conductivity of the treatment liquid,
        concentration of at least one substance in the treatment liquid;
        receiving at least one prescription value for the characteristic;
        causing a plurality of consecutive and continuously repeated variations of the characteristic around the prescription value in the liquid flowing in the preparation line, each one of said variations being obtained by:
        changing the value of the characteristic in the preparation line until a first inlet value of the characteristic is reached, said first value being different from the prescription value,
        keeping the characteristic in the preparation line unchanged at said first inlet value during a first time interval,
        changing the value of the characteristic in the preparation line until a second inlet value of the characteristic is reached, wherein the second inlet value is different than the prescription value and the prescription value is comprised between said first and said second inlet values,
        keeping the characteristic in the preparation line unchanged at said second inlet value during a second time interval following the first time interval,
        during each of said variations the characteristic in the liquid flowing in the preparation line taking the first inlet value during the first time interval and taking the second inlet value during the second time interval;
        for of each of said variations:
            receiving measures of a first and second outlet values respectively adopted by the characteristic in the spent dialysate line in response to the first and second inlet values taken by the same characteristic in the preparation line, and
            computing at least one value of a parameter indicative of the effectiveness of the extracorporeal blood treatment from said first and second outlet values taken by the characteristic in the spent dialysate line.

2. Apparatus according to claim 1, wherein the step of causing a plurality of consecutive and continuously repeated variations of the characteristic around the prescription value is configured such that, taking as base line the line defined over time by the prescribed value, the sum of the areas formed between said base line and the portions of curve representative of the inlet conductivity/concentration positioned above the base line is identical or close to the sum of the areas defined between the base line and the portions of curve representative of the inlet conductivity/concentration curve positioned below the base line.

3. Apparatus according to claim 1, wherein the step of causing a plurality of consecutive and continuously repeated variations of the characteristic around the prescription value is configured such as to define a sequence of variations symmetrically evolving over time around the prescribed value.

4. Apparatus according to claim 1, wherein the first time interval and the second time interval of each variation have same duration, and wherein the first and second inlet values in each variation differ from the prescribed value by a same quantity.

5. Apparatus according to claim 1, wherein the control unit is further configured for receiving a total treatment time, and wherein said variations of the characteristic around the prescription value are consecutively and continuously repeated during a significant portion of the treatment time such that a plurality of values of the parameter indicative of the effectiveness of the extracorporeal blood treatment are correspondingly determined,
    said significant portion of the treatment time comprising one in the group of:
    at least 25% of said treatment time,
    at least 50% of said treatment time,
    at least 75% of said treatment time,
    the entire treatment time.

6. Apparatus according to claim 1, wherein:
    each first time interval and each second time interval in each variation are preset values, longer than 2 minutes and shorter than 6 minutes, and the first and second inlet values in each variation are preset values differing from the prescribed value by a quantity comprised between 0.3 and 1 mS/cm.

7. Apparatus according to claim 1, wherein changing the value of the characteristic in the preparation line until a first inlet value of the characteristic is reached comprises a step increase or a step decrease of the characteristic, and wherein changing the value of the characteristic in the preparation line until a second inlet value of the characteristic is reached comprises a step decrease or a step increase of the characteristic such that the consecutive and continuously repeated variations define a square wave.

8. Apparatus according to claim 1, wherein at each variation said change of the value of the characteristic until a first inlet value is reached is an increase of the value of the characteristic above the prescription value or a decrease of the value of the characteristic below the prescription value, and
wherein at each variation said change of the value of the characteristic until a second inlet value is reached is a decrease of the value of the characteristic below the prescription value when the first value is above the prescription value or an increase of the value of the characteristic above the prescription value when the first inlet value is below the prescription value.

9. Apparatus according to claim 1, wherein said parameter comprises one selected in the group of:
an effective dialysance for one or more substances of the treatment unit,
an effective clearance for one or more substances of the treatment unit,
a concentration of a substance in blood upstream the blood treatment unit,
a dialysis dose at time after start of the treatment.

10. Apparatus according to claim 1, wherein the parameter comprises the effective dialysance and wherein each computed value of said parameter for the respective variation is obtained using the formula:

$$D_k = 500 \cdot [(Cd_{in1} - Cd_{out1}) + (Cd_{in2} - Cd_{out2})] / (Cd_{in1} - Cd_{in2})$$

where:
$Cd_{out1}$ is the first outlet value taken by the characteristic in the spent dialysate line downstream of the secondary chamber in response to the change of characteristic in the preparation line to said first inlet value $Cd_{in1}$,
$Cd_{out2}$ is the second value taken by the characteristic in the spent dialysate line downstream of the secondary chamber in response to the change of characteristic in the preparation line at said second inlet value,
$Cd_{in1}$, $Cd_{in2}$ are first and second inlet values taken by the characteristic in the preparation line upstream of the secondary chamber.

11. Apparatus according to claim 10, wherein the parameter comprises a concentration of a substance in blood upstream the blood treatment unit, and wherein each computed value of said parameter for the respective variation is obtained using the formula:

$$Cb_{in(k)} = [(500 \cdot Cd_{out2}) - (D_k \cdot Cd_{in2})] / (500 - D_k),$$

where $D_k$ is calculated using the formula of claim 10.

12. Apparatus according to claim 1, wherein the control unit is configured for executing a validation routine in connection to each calculated value of the parameter, the validation routine comprising the following steps:
determining from a plurality of calculated values of the parameter a trend over time of the same parameter;
establishing when one or more of the calculated values of the parameter deviates from the determined trend;
discard as invalid the calculated values deviating from the determined trend.

13. Apparatus according to the preceding claim 12, wherein determining said trend comprises determining an ideal curve representative of a plurality of calculated values of the parameter, and wherein establishing when one or more of the calculated values deviates from the trend comprises comparing each calculated value of the parameter with the ideal curve and verifying if the calculated value differs from values of the curve by more than a prescribed threshold.

14. Apparatus according to claim 1,
wherein the control unit is configured for determining calculated values of at least a first and a second parameters indicative of the effectiveness of the extracorporeal blood treatment and wherein the control unit is configured for:
determining a trend over time of a first parameter from a plurality of calculated values taken by said first parameter,
determining a trend over time of a second parameter from a plurality of calculated values taken by said second parameter,
establishing if the calculated values of the first and second parameters deviate from the respective determined trend in correspondence of a same time interval,
discarding the calculated values of the first and second parameters deviating from the respective trend in correspondence of a same time interval;
or wherein the control unit is configured for determining calculated values of at least a first and a second parameters indicative of the effectiveness of the extracorporeal blood treatment and wherein the control unit is configured for:
determining a trend over time of a first parameter from a plurality of calculated values taken by said first parameter,
determining a trend over time of a second parameter from a plurality of calculated values taken by said second parameter,
establishing if the calculated values of the first and second parameters deviate from the respective determined trend and in the affirmative:
a) verifying whether one or both of the first and second parameters deviate from the respective trend in correspondence of a same time or time interval,
b) whether the deviation is temporary or lasts for the rest of the treatment,
identifying a potential cause of the deviation based on factors a) and b);
further wherein the first parameter is one of the effective dialysance for at least one substance, and the effective clearance for at least one substance; and the second parameter is one of the blood conductivity or the plasma conductivity upstream the blood treatment unit.

15. Apparatus according to claim 1, comprising said treatment unit, wherein:
the preparation line has one end connected to an inlet of the secondary chamber of the treatment unit,
the spent dialysate line has one end connected to the outlet of said secondary chamber,
a blood withdrawal line is connected at an inlet of the primary chamber and
a blood return line is connected at an outlet of the primary chamber.

16. A method of controlling an apparatus for extracorporeal treatment of blood, the apparatus being of the type comprising:
- a preparation line having one end configured for being connected to an inlet of a secondary chamber of a treatment unit having a primary chamber and said secondary chamber separated by a semi-permeable membrane;
- a spent dialysate line having one end configured for being connected to an outlet of said secondary chamber;
- the method comprising execution of the following steps:
  - causing a treatment liquid to flow in the preparation line to the secondary chamber, the treatment liquid having a characteristic which is one selected in the group of:
  - conductivity of the treatment liquid,
  - concentration of at least one substance in the treatment liquid;
  - receiving at least one prescription value for the characteristic;
  - causing a plurality of consecutive and continuously repeated variations of the characteristic around the prescription value in the liquid flowing in the preparation line, each one of said variations being obtained by:
    - changing the value of the characteristic in the preparation line until a first inlet value of the characteristic is reached, said first value being different from the prescription value,
    - keeping the characteristic in the preparation line unchanged at said first inlet value during a first time interval,
    - changing the value of the characteristic in the preparation line until a second inlet value of the characteristic is reached, wherein the second inlet value is different than the prescription value and the prescription value is comprised between said first and said second inlet values,
    - keeping the characteristic in the preparation line unchanged at said second inlet value during a second time interval, following the first time interval,
  - during each of said variations the characteristic in the liquid flowing in the preparation line taking the first inlet value during the first time interval and taking the second inlet value during the second time interval;
  - for of each of said variations:
    - receiving measures of a first and second outlet values respectively adopted by the characteristic in the spent dialysate line in response to the first and second inlet values taken by the same characteristic in the preparation line, and
    - computing at least one value of a parameter indicative of the effectiveness of the extracorporeal blood treatment from said first and second outlet values taken by the characteristic in the spent dialysate line.

17. A method according to claim 16 wherein the first time interval and the second time interval of each variation have same duration and wherein the first and second inlet values in each variation differ from the prescribed value by a same quantity.

18. A method according to claim 16, wherein the first and second inlet values in each variation differ from the prescribed value by a same quantity comprised between 0.3 and 1 mS/cm, the first and second inlet values in each variation define a sequence of variations symmetrically evolving around the prescribed value.

19. A method according to claim 16, wherein said variations of the characteristic around the prescription value are consecutively and continuously repeated during a significant portion of a treatment time such that a plurality of values of the parameter indicative of the effectiveness of the extracorporeal blood treatment are correspondingly determined, wherein said significant portion of the treatment time is at least 25% of said treatment time or at least 50% of said treatment time or at least 75% of said treatment time or the entire treatment time and wherein each first time interval and each second time interval in each variation is longer than 2 minutes and shorter than 6 minutes.

20. A method according to claim 16, wherein changing the value of the characteristic in the preparation line until a first inlet value of the characteristic is reached comprises a step increase or a step decrease of the characteristic, and wherein changing the value of the characteristic in the preparation line until a second inlet value of the characteristic is reached comprises a step decrease or a step increase of the characteristic such that the consecutive and continuously repeated variations define a square wave.

21. A method according to claim 16, wherein at each variation said change of the value of the characteristic until a first inlet value is reached is an increase of the value of the characteristic above the prescription value or a decrease of the value of the characteristic below the prescription value.

22. A method according to claim 16, wherein at each variation said change of the value of the characteristic until a second inlet value is reached is a decrease of the value of the characteristic below the prescription value when the first value is above the prescription value or an increase of the value of the characteristic above the prescription value when the first inlet value is below the prescription value.

23. A method according to claim 16, wherein said parameter comprises one selected in the group of:
- an effective dialysance for one or more substances of the treatment unit,
- an effective clearance for one or more substances of the treatment unit,
- a concentration of a substance in blood upstream the blood treatment unit,
- a dialysis dose at time after start of the treatment.

24. A method according to claim 16, wherein the parameter comprises the effective dialysance, each computed value of said parameter for the respective variation being obtained using the formula:

$$D_k = 500 \cdot [(Cd_{in1} - Cd_{out1}) + (Cd_{in2} - Cd_{out2})]/(Cd_{in1} - Cd_{in2})$$

where:
- $Cd_{out1}$ is the first outlet value taken by the characteristic in the spent dialysate line downstream of the secondary chamber in response to the change of characteristic in the preparation line to said first inlet value $Cd_{in1}$,
- $Cd_{out2}$ is the second value taken by the characteristic in the spent dialysate line downstream of the secondary chamber in response to the change of characteristic in the preparation line at said second inlet value,
- $Cd_{in1}$, $Cd_{in2}$ are first and second inlet values taken by the characteristic in the preparation line upstream of the secondary chamber.

25. A method according to the preceding claim 24, wherein the parameter comprises a concentration of a substance in blood upstream the blood treatment unit, each computed value of said parameter for the respective variation being obtained using the formula:

$$Cb_{in(k)} = [(500 \cdot Cd_{out2}) - (D_k \cdot Cd_{in2})]/(500 - D_k),$$

where $D_k$ is calculated using the formula of claim 24.

26. A method according to claim 16, wherein the method comprises executing a validation routine in connection to each calculated value of the parameter, the validation routine comprising the following steps:
determining from more than 5 calculated values of the parameter a trend over time of the same parameter;
establishing when one or more of the calculated values of the parameter deviates from the determined trend;
discarding as invalid the calculated values deviating from the determined trend,
wherein determining said trend comprises determining an ideal curve representative of a plurality of calculated values of the parameter, and wherein establishing when one or more of the calculated values deviates from the trend comprises comparing each calculated value of the parameter with the ideal curve and verifying if the calculated value differs from values of the curve by more than a prescribed threshold.

27. A method according to claim 16, wherein the method comprises determining calculated values of at least a first and a second parameters indicative of the effectiveness of the extracorporeal blood treatment, said method further comprising the steps of:
determining a trend over time of a first parameter from a plurality of calculated values taken by said first parameter,
determining a trend over time of a second parameter from a plurality of calculated values, taken by said second parameter,
establishing if the calculated values of the first and second parameters deviate from the respective determined trend in correspondence of a same time interval,
discarding the calculated values of the first and second parameters deviating from the respective trend in correspondence of a same time interval, wherein the first parameter is one of the effective dialysance for at least one substance, and the effective clearance for at least one substance; and the second parameter is one of the blood conductivity or the plasma conductivity upstream the blood treatment unit.

28. A method according to claim 16, wherein the method comprises determining calculated values of at least a first and a second parameters indicative of the effectiveness of the extracorporeal blood treatment, said method further comprising the steps of:
determining a trend over time of a first parameter from a plurality of calculated values taken by said first parameter,
determining a trend over time of a second parameter from a plurality of calculated values taken by said second parameter,
establishing if the calculated values of the first and second parameters deviate from the respective determined trend and in the affirmative:
a) verifying whether one or both of the first and second parameters deviate from the respective trend in correspondence of a same time or time interval,
b) whether the deviation is temporary or lasts for the rest of the treatment,
identifying a potential cause of the deviation based on factors a) and b),
wherein the method provides for associating at least a first cause if both the first and second parameters deviate from the respective trend in correspondence of a same time or time interval, and at least a second cause different from the first cause if only one of the first and second parameters deviate from the respective trend in correspondence of a same time or time interval, wherein the first parameter is one of the effective dialysance for at least one substance, and the effective clearance for at least one substance; and the second parameter is one of the blood conductivity or the plasma conductivity upstream the blood treatment unit.

29. A method according to claim 16, wherein the step of causing a plurality of consecutive and continuously repeated variations of the characteristic around the prescription value is configured such that, taking as base line the line defined over time by the prescribed value, the sum of the areas formed between said base line and the portions of curve representative of the inlet conductivity/concentration positioned above the base line is identical or close to the sum of the areas defined between the base line and the portions of curve representative of the inlet conductivity/concentration curve positioned below the base line, This allows the respect of the prescription value across the treatment irrespective of the continuous conductivity/concentration variations imposed to the inlet conductivity.

30. A method according to claim 16, wherein the consecutive variations are caused one immediately after the other such that the characteristic defines a plurality of continuously and immediately repeated variations of the characteristic around the prescription value in the liquid flowing in the preparation line.

* * * * *